(12) United States Patent
Nieto-Roman et al.

(10) Patent No.: US 8,003,799 B2
(45) Date of Patent: Aug. 23, 2011

(54) PICOLINIC ACID DERIVATIVES AND THEIR USE AS FUNGICIDES

(75) Inventors: Francisco Nieto-Roman, Palencia (ES); Jean-Pierre Vors, Lyons (FR); Alain Villier, Saint Didier au Mont d'Or (FR); Helene Lachaise, Lyons (FR); Adeline Mousques, Lyons (FR); Benoit Hartmann, Sainte-Foy-les-Lyon (FR); Pierre Hutin, Lyons (FR); Jose Lorenzo Molina, Munich (DE); Benoit Muller, Lyons (FR)

(73) Assignee: Bayer SAS (FR)

( * ) Notice: Subject to any disclaimer, the term of this patent is extended or adjusted under 35 U.S.C. 154(b) by 813 days.

(21) Appl. No.: 10/181,842

(22) PCT Filed: Jan. 5, 2001

(86) PCT No.: PCT/FR01/00033
§ 371 (c)(1),
(2), (4) Date: Jul. 8, 2002

(87) PCT Pub. No.: WO01/49666
PCT Pub. Date: Jul. 12, 2001

(65) Prior Publication Data
US 2003/0191113 A1    Oct. 9, 2003

(30) Foreign Application Priority Data
Jan. 6, 2000 (FR) .................................... 00 00140

(51) Int. Cl.
| C07D 213/00 | (2006.01) |
| C07D 241/36 | (2006.01) |
| A01N 57/18 | (2006.01) |
| A01N 43/60 | (2006.01) |
| A01N 43/40 | (2006.01) |
| A01N 47/28 | (2006.01) |
| A01N 37/18 | (2006.01) |

(52) U.S. Cl. ........ 546/309; 544/349; 514/141; 514/142; 514/249; 514/354; 504/148; 504/149

(58) Field of Classification Search .................. 546/309; 544/349; 514/249, 354, 141, 142; 504/141, 504/142, 148, 149
See application file for complete search history.

(56) References Cited

U.S. PATENT DOCUMENTS

| 3,228,950 | A |   | 1/1966  | Ernst et al. |
| 4,535,060 | A |   | 8/1985  | Comai ....................... 435/172.3 |
| 4,715,888 | A | * | 12/1987 | Marzolph et al. ............. 504/134 |
| 4,752,608 | A | * | 6/1988  | Katoh et al. .................. 514/269 |
| 4,769,061 | A |   | 9/1988  | Comai .............................. 71/86 |
| 4,940,835 | A |   | 7/1990  | Shah et al. .................... 800/205 |
| 4,971,908 | A |   | 11/1990 | Kishore et al. ............. 435/172.1 |
| 5,094,945 | A |   | 3/1992  | Comai ....................... 435/172.3 |
| 5,145,783 | A |   | 9/1992  | Kishore et al. ............. 435/320.1 |
| 5,188,642 | A |   | 2/1993  | Shah et al. ......................... 47/58 |
| 5,208,239 | A | * | 5/1993  | Robson et al. ................ 514/256 |
| 5,250,530 | A | * | 10/1993 | Giencke et al. ............... 514/256 |
| 5,250,533 | A | * | 10/1993 | Heinemann et al. .......... 514/256 |
| 5,310,667 | A |   | 5/1994  | Eichholtz et al. .......... 435/172.3 |
| 5,312,910 | A |   | 5/1994  | Kishore et al. ............... 536/23.2 |
| 5,506,195 | A |   | 4/1996  | Ensminger et al. ........... 504/350 |
| 5,510,471 | A |   | 4/1996  | Lebrun et al. ................ 536/23.4 |
| 5,616,590 | A | * | 4/1997  | Maetzke ....................... 514/301 |
| 5,627,061 | A |   | 5/1997  | Barry et al. ................. 438/172.3 |
| 5,633,435 | A |   | 5/1997  | Barry et al. ................... 800/205 |
| 5,658,933 | A | * | 8/1997  | Weidmann et al. ........... 514/350 |
| 6,521,622 | B1 | * | 2/2003 | Ricks et al. ............... 514/252.01 |
| 7,084,163 | B2 |   | 8/2006  | Gary et al. |
| 2004/0142977 | A1 | * | 7/2004 | Hutin et al. .................... 514/341 |
| 2004/0147514 | A1 | * | 7/2004 | Muller et al. ............... 514/235.2 |
| 2004/0152698 | A1 | * | 8/2004 | Gary et al. .................. 514/227.8 |
| 2006/0040995 | A1 | * | 2/2006 | Bacque et al. ................ 514/350 |

FOREIGN PATENT DOCUMENTS

| DE | 19958166 |   | 12/2000 |
| EP | 0496630  |   | 7/1992 |
| EP | 0496631  |   | 7/1992 |
| EP | 0625505  |   | 11/1994 |
| EP | 0625508  |   | 11/1994 |
| EP | 650961   | * | 5/1995 |
| FR | 2727206  |   | 5/1996 |
| FR | 2734840  |   | 12/1996 |

(Continued)

OTHER PUBLICATIONS

Nora, Marcus et. al., "Ortho-Directed Lithiation Studies of 4-chloro-picolinanilide: Introduction of Functional Groups at C-3 and their elaboration to Chain Extended Derivatives via Carbon-Carbon Bond formation", Heterocycles, vol. 47, No. 2, 1998.*

(Continued)

*Primary Examiner* — Janet Andres
*Assistant Examiner* — Heidi Reese
(74) *Attorney, Agent, or Firm* — Ostrolenk Faber LLP

(57) ABSTRACT

Compounds of general formula (I):

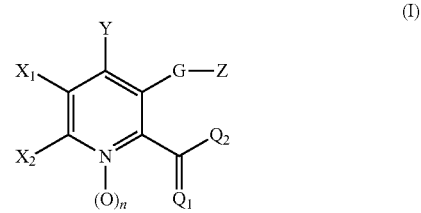

in which n, G, $Q_1$, $Q_2$, $X_1$, $X_2$, Y and Z are as defined in the description, process for preparing these compounds, fungicidal compositions comprising these compounds, processes for treating plants by applying these compounds or compositions.

13 Claims, No Drawings

FOREIGN PATENT DOCUMENTS

| | | |
|---|---|---|
| FR | 7736926 | 1/1997 |
| JP | 2-1484 | 1/1990 |
| JP | 7-228571 | 8/1995 |
| JP | 7-242635 | 9/1995 |
| JP | 8-053464 | 2/1996 |
| JP | 10-259181 * | 10/1998 |
| JP | 11-228542 | 8/1999 |
| WO | 9102071 | 2/1991 |
| WO | 9214822 | 9/1992 |
| WO | 9306712 | 4/1993 |
| WO | WO 93/22311 | 11/1993 |
| WO | 9420828 | 9/1994 |
| WO | 9506128 | 3/1995 |
| WO | 95/25723 | 9/1995 |
| WO | 9531554 | 11/1995 |
| WO | 9638567 | 12/1996 |
| WO | 9717432 | 5/1997 |
| WO | 9741239 | 11/1997 |
| WO | 9808932 | 3/1998 |
| WO | 9820133 | 5/1998 |
| WO | WO 99/02518 | 1/1999 |
| WO | 9911127 | 3/1999 |
| WO | 00/26191 | 5/2000 |
| WO | 01/05769 | 1/2001 |
| WO | 01/14339 | 3/2001 |
| WO | WO 01/14339 | 3/2001 |
| WO | WO 01/49667 | 7/2001 |

OTHER PUBLICATIONS

Donati et. al., "Pothochemical Rearrangements of 3-methylisoxalolopyridines", Heterocycles, vol. 27, No. 8, 1988.*
Hcaplus 124:232468.*
Hcaplus 1965:488771, "Preparation of derivatives of 3-hydroxypicolinic acid from furfural", 1965, Clauson-Kaas, Niels et. al.*
Zcaplus 1983:522241, (1983), Johnsen et. al.*
Sakanaka et. al., "Novel antifungal compounds and process for producing the same", Hcaplus 1999:511149, 1999.*
"*The Journal of Antibiotics*", vol. 51, No. 12, Dec. 1998, pp. 1113-1116, by Kuzo Shitaba, et al.
"*Advanced Organic Chemistry*", Reactions, Mechanisms, and Structure, Fourth Edition, by Jerry March, published by Wiley (1992) ibid, pp. 1200, 1219-1220.
"*Heterocycles*", vol. 47, No. 2, 1998, pp. 811-827, by Marcus V. Nora and Robert H. Dodd.
M.V. Nora de Souza et al., "Ortho-Directed Lithiation Studies of 4-Chloro-picolinanilide . . . ," 47(2) Heterocycles 811-27 (1998).
D. Donati et al., "Photochemical Rearrangements of 3-Methylisoxazolopyridines," 27(8) Hetercycles 1899-1905 (1988).
C. Kaneko et al., "The Isomerization of 1aH-Oxazirino[2,3-a]quinoline 1a-carbonitrile and Its Substituted Derivatives . . . ," 15(5) Chem. Pharm. Bull. 663-69 (1967).
Niels Clauson-Kaas et al., "Preparation of Derivatives of 3-Hydroxypicolinic Acid from Furfural," 19(5) Acta. Chem. Scand. 1147-52.

* cited by examiner

PICOLINIC ACID DERIVATIVES AND THEIR USE AS FUNGICIDES

This application is a 371 of PCT/FR01/00033 filed Jan. 5, 2001

The present invention relates to new derivatives of picolinic acid, their process of preparation, their use as fungicides, particularly in the form of fungicidal compositions, and methods for the control of phytopathogenic fungi of plants using these compounds or their compositions.

Picolinic acid derivatives with fungicidal action are known in the literature. Thus, antimycin and certain derivatives thereof, disclosed in particular in patent application WO-A-99/11127 and by Kuzo Shibata et al. (*The Journal of Antibiotics*, 51 (12), (1998), 1113-1116), are presented as being effective against phytopathogenic fungi of plants, with good efficacy. These compounds, and also those disclosed in U.S. Pat. No. 3,228,950, have no substituents in position 4 of the pyridine nucleus.

Patent application WO-A-00/26191 presents picolinamide derivatives that are optionally substituted in position 4 with a methoxy radical. Patent application WO-A-95/25723 proposes 3-pyridylcarboxylic acid derivatives.

However, these known compounds have the drawback of being toxic products, which forbids any use of these compounds in agriculture for eradicating phytopathogenic diseases of crops. Furthermore, these compounds are obtained from fermentation musts and have relatively complex chemical structures. Thus, the preparations and purifications of these compounds remain demanding and expensive operations, making any industrial synthesis or marketing economically non-viable.

Picolinamide derivatives are also known from patent application publication JP-11 228 542. These derivatives are presented as having potential antifungal activities and low toxicity, for use in pharmaceutical products. Other picolinic acid derivatives are also known from patent application EP-A-0 690 061, in which such compounds are used as synthetic intermediates for the preparation of pyridothiadiazoles.

Thus, a first object of the present invention comprises a new family of picolinic acid derivatives not possessing previously cited disadvantages.

Another object of the present invention is to propose a new family of compounds having an improved activity, both quantitatively and qualitatively, in comparison with the known fungicides, antimycin or derivatives. By activity, is meant fungicidal activity; by quantitative improvement, is understood a better control of phytopathogenic fungi on plants and, by qualitative improvement, a broader spectrum of activity, that is to say control of a greater variety of phytopathogenic fungi of plants.

Another object of the present invention is to provide a new family of compounds having an improved toxicity and/or phytotoxicity and/or ecotoxicity in comparison with known fungicides, particularly antimycin and its derivatives.

Another object of the present invention is to provide a new family of compounds possessing the characteristics indicated above, notably on crops such as cereals, rice, corn, fruit trees, woodland trees, vines, oil-yielding plants, protein-yielding plants, market garden crops, solanaceous crops, beet, flax, citrus fruits, banana, ornamental plants and tobacco.

Another object of the present invention is to provide a new family of picolinic acid derivatives possessing the characteristics indicated above, notably on crops such as cereals, rice, corn, fruit trees, woodland trees, vine, oil-yielding plants, protein-yielding plants, market garden plants, solanaceous plants, beet, flax, citrus fruits, banana and ornamental plants and tobacco.

Another object of the present invention consists equally in proposing a new family of picolinic acid derivatives useful for the treatment and protection of lumber against fungal disease. In effect, lumber used for example for the fabrication of buildings and furniture (framework, walls, ceilings, flooring etc.), may suffer different injuries, among others, due to phytopathogenic fungi. The compounds according to the present invention allow these attacks to be combated.

Another object of the present invention comprises proposing a new family of picolinic acid derivatives useful in human and animal therapy. In fact, by virtue of their antifungal properties, the picolinic acid derivatives which are the object of the present invention can prove useful for the treatment, in man and animals, of fungal diseases, such as for example mycosis and candidacies.

Surprisingly it has been found that these objects can be achieved in whole or in part, by picolinic acid derivatives such as those described in the present invention.

GENERAL DEFINITION OF INVENTION

The invention relates to picolinic acid derivatives of general formula (I):

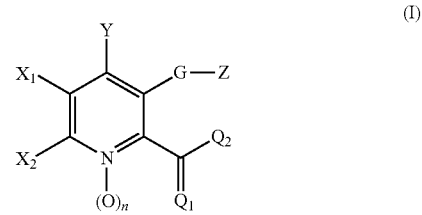

in which:
G represents an oxygen or sulphur atom,
n represents 0 or 1,
$Q_1$ is chosen from an oxygen or sulphur atom, a group $NR_1$ and a group $N-NR_4R_5$,
$Q_2$ is chosen from a group $OR_2$ or $SR_3$ and a group $-NR_4R_5$, or
$Q_1$ and $Q_2$ may together form a ring of 5 to 7 atoms containing 2 to 3 oxygen and/or nitrogen atoms, optionally substituted with one or more radicals, which may be identical or different, chosen from halogens and alkyl and haloalkyl radicals,
Z is chosen from a hydrogen atom, a cyano radical and an alkyl, allyl, aryl, arylalkyl, propargyl, cycloalkyl, halocycloalkyl, alkenyl, alkynyl, cyanoalkyl, haloalkyl, alkoxyalkyl, haloalkoxyalkyl, alkylthioalkyl, haloalkylthioalkyl, N-alkylaminoalkyl, N,N-dialkylaminoalkyl, acylaminoalkyl, alkoxycarbonylaminoalkyl, aminocarbonylaminoalkyl, alkoxycarbonyl, N-alkylaminocarbonyl, N,N-dialkylaminocarbonyl, acyl, thioacyl, alkoxythiocarbonyl, N-alkylaminothiocarbonyl, N,N-dialkylaminothiocarbonyl, alkylsulphinyl, haloalkylsulphinyl, alkylsulphonyl, haloalkylsulphonyl, alkoxysulphonyl, aminosulphonyl, N-alkylaminosulphonyl, N,N-dialkylaminosulphonyl, arylsulphinyl, arylsulphonyl, aryloxysulphonyl, N-arylaminosulphonyl, N,N-diarylaminosulphonyl or N,N-arylalkylaminosulphonyl radical;

Y is chosen from a halogen atom, a hydroxyl, mercapto, nitro, thiocyanato, azido, cyano or pentafluorosulphonyl radical, an alkyl, haloalkyl, alkylthio, haloalkylthio, alkoxyalkyl, haloalkoxyalkyl, alkylthioalkyl, haloalkylthioalkyl, cyanoalkyl, cyanoalkoxy, cyanoalkylthio, alkylsulphinyl, haloalkylsulphinyl, alkylsulphonyl, haloalkylsulphonyl or alkoxysulphonyl radical, a cycloalkyl, halocycloalkyl, alkenyl, alkynyl, alkenyloxy, alkynyloxy, alkenylthio or alkynylthio group, an amino, N-alkylamino, N,N-dialkylamino, —NHCOR$_{10}$, —NHCSR$_{10}$, N-alkylaminocarbonylamino, N,N-dialkylaminocarbonylamino, aminoalkyl, N-alkylaminoalkyl, N,N-dialkylaminoalkyl, acylaminoalkyl, thioacylamino, alkoxythiocarbonylamino, N-alkylaminothiocarbonylamino, N,N-dialkylaminothiocarbonylamino, N,N-arylalkylaminocarbonylamino, N-alkylsulphinylamino, N-alkylsulphonylamino, N-alkyl(alkylsulphonyl)amino, N-arylsulphinylamino, N-arylsulphonylamino, N-alkoxysulphonylamino, N-alkoxysulphinylamino, N-haloalkoxysulphinylamino, N-haloalkoxysulphonylamino, N-arylamino, N,N-diarylamino, arylcarbonylamino, alkoxycarbonylamino, N-arylaminocarbonylamino, N,N-diarylaminocarbonylamino, arylthiocarbonylamino, aryloxythiocarbonylamino, N-arylaminothiocarbonylamino, N,N-diarylaminothiocarbonylamino or N,N-arylalkylaminothiocarbonylamino group, an acyl, carboxyl, carbamoyl, N-alkylcarbamoyl, N,N-dialkylcarbamoyl, lower alkoxycarbonyl, N-arylcarbamoyl, N,N-diarylcarbamoyl, aryloxycarbonyl or N,N-arylalkylcarbamoyl radical, and an imino group of formula:

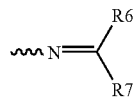

X$_1$ and X$_2$ are identical or different and chosen, independently of each other, from a hydrogen atom, a halogen atom, a hydroxyl, mercapto, nitro, thiocyanato, azido, cyano or pentafluorosulphonyl radical, and an alkyl, haloalkyl, alkoxy, haloalkoxy, alkylthio, haloalkylthio, alkoxyalkyl, haloalkoxyalkyl, alkylthioalkyl, haloalkylthioalkyl, cyanoalkyl, cyanoalkoxy, cyanoalkylthio, alkylsulphinyl, haloalkylsulphinyl, alkylsulphonyl, haloalkylsulphonyl or alkoxysulphonyl radical, or X$_1$ and X$_2$ may also be joined together, thus forming a saturated, partially unsaturated or totally unsaturated 4- to 8-membered ring optionally comprising one or more hetero atoms chosen from sulphur, oxygen, nitrogen and phosphorus, R$_2$ and R$_3$ are identical or different and chosen, independently of each other, from an alkyl radical comprising from 1 to 12 carbon atoms, a haloalkyl, cycloalkyl, halocycloalkyl, alkoxy, haloalkoxy, alkylthio, haloalkylthio, alkoxyalkyl, haloalkoxyalkyl, alkylthioalkyl, haloalkylthioalkyl, cyanoalkyl or acyl radical, a nitro, cyano, carboxyl, carbamoyl or 3-oxetanyloxycarbonyl radical, and an N-alkylcarbamoyl, N,N-dialkylcarbamoyl, alkoxycarbonyl, alkylthiocarbonyl, haloalkoxycarbonyl, alkoxythiocarbonyl, haloalkoxythiocarbonyl, alkylthiothiocarbonyl, alkenyl, alkynyl, N-alkylamino, N,N-dialkylamino, N-alkylaminoalkyl or N,N-dialkylaminoalkyl radical, or a radical chosen from aryl, arylalkyl, heterocyclyl and heterocyclylalkyl, optionally substituted with one or more radicals R$_9$ and/or aryl and/or arylalkyl, which may be identical or different, and/or a group -T-R$_8$, or R$_1$, R$_4$, R$_5$, R$_6$ and R$_7$ are identical or different and chosen, independently of each other, from a hydrogen atom, an optionally substituted alkyl radical comprising from 1 to 12 carbon atoms in a linear or branched chain, a haloalkyl, cycloalkyl, halocycloalkyl, alkoxy, aryloxy, arylalkoxy, haloalkoxy, alkylthio, haloalkylthio, alkoxyalkyl, haloalkoxyalkyl, alkylthioalkyl, haloalkylthioalkyl, cyanoalkyl or acyl radical, a nitro, cyano, carboxyl, carbamoyl or 3-oxetanyloxycarbonyl radical, and an N-alkylcarbamoyl, N,N-dialkylcarbamoyl, alkoxycarbonyl, alkylthiocarbonyl, haloalkoxycarbonyl, alkoxythiocarbonyl, haloalkoxythiocarbonyl, alkylthiothiocarbonyl, alkenyl, alkynyl, N-alkylamino, N,N-dialkylamino, N-alkylaminoalkyl or N,N-dialkylaminoalkyl radical, or a radical chosen from aryl, arylalkyl, heterocyclyl and heterocyclylalkyl, optionally substituted with one or more radicals R$_9$ and/or aryl and/or arylalkyl, which may be identical or different, and/or a group -T-R$_8$, or R$_4$ and R$_5$, on the one hand, or R$_6$ and R$_7$, on the other hand, may be joined together, thus forming a saturated, partially unsaturated or totally unsaturated 4- to 8-membered ring optionally comprising one or more hetero atoms chosen from sulphur, oxygen, nitrogen and phosphorus, T represents a direct bond or a divalent radical chosen from a radical —(CH$_2$)$_m$—, m taking a value between 1 and 12, limits included, the said radical optionally being interrupted or ending with one or two hetero atoms chosen from nitrogen, oxygen and/or sulphur, and an oxyalkylene, alkoxyalkylene, carbonyl (—CO—), oxycarbonyl (—O—CO—), carbonyloxy (—CO—O—), sulphinyl (—SO—), sulphonyl (—SO$_2$—), oxysulphonyl (—O—SO$_2$—), sulphonyloxy (—SO$_2$—O—), oxysulphinyl (—O—SO—), sulphinyloxy (—SO—O—), thio (—S—), oxy (—O—), vinyl (—C=C—), ethynyl (—C≡C—), —NR$_9$—, —NR$_9$O—, —ONR$_9$—, —N=N—, —NR$_9$—NR$_{10}$—, —NR$_9$—S—, —NR$_9$—SO—, —NR$_9$—SO$_2$—, —S—NR$_9$—, —SO—NR$_9$—, —SO$_2$—NR$_9$—, —CO—NR$_9$—O— or —O—NR$_9$—CO— radical, R$_8$ is chosen from a hydrogen atom and an aryl or heterocyclyl radical, R$_9$ and R$_{10}$, which may be identical or different, are chosen, independently of each other, from a hydrogen atom, a halogen atom, a hydroxyl, mercapto, nitro, thiocyanato, azido, cyano or pentafluorosulphonyl radical, and an alkyl, haloalkyl, alkoxy, haloalkoxy, alkylthio, haloalkylthio, alkoxyalkyl, haloalkoxyalkyl, alkylthioalkyl, haloalkylthioalkyl, arylalkyl, cyanoalkyl, cyanoalkoxy, cyanoalkylthio, alkylsulphinyl, haloalkylsulphinyl, alkylsulphonyl, haloalkylsulphonyl or alkoxysulphonyl radical, as well as the optional N-oxides, geometrical and/or optical isomers, enantiomers and/or diastereoisomers, tautomeric forms, salts and metal and metalloid complexes of the compounds of formula (I) as have just been defined, with the restriction that when Q$_1$ represents oxygen, G-Z represents a dialkylaminocarbonyloxy or dialkylaminothiocarbonyloxy radical, Y represents an NH$_2$ radical or an N$_3$ radical, Q$_2$ represents a radical —NR$_4$R$_5$ and R$_4$ represents an alkyl radical comprising from 1 to 12 carbon atoms, then $R_5$ cannot represent an alkyl radical comprising from 1 to 12 carbon atoms.

The tautomeric forms of the compounds of formula (I) such as those defined above are also included in the invention. By tautomeric forms there are to be understood all of the isomeric forms described in the work "The Tautomerism of Heterocycles, Advances in Heterocyclic Chemistry, Supplement 1, by J Elguero, C. Martin, A. R. Katritsky and P Linda, published by Academic Press, New York, 1976, pages 1-4.

The following generic terms are used with the following meanings:

halogen atom signifies the fluorine, chlorine, bromine or iodine atom, the alkyl radicals as well as groups including these alkyl radicals (alkoxy, alkylcarbonyl or acyl, etc.) include, unless indicated to the contrary, from 1 to 6 carbons atoms in a linear or branched chain and are optionally substituted, the halogenated alkyl, alkoxy and halocycloalkyl radicals may comprise one or more identical or different halogen atoms, the cycloalkyl radicals comprise from 3 to 6 carbon atoms and are optionally substituted, the alkenyl and alkynyl radicals, as well as groups including such radicals, comprise, unless indicated to the contrary, from 2 to 6 carbon atoms in a straight or branched chain and are optionally substituted, the acyl radical signifies alkylcarbonyl or cycloalkylcarbonyl, the alkyl part containing from 1 to 6 carbon atoms and the cycloalkyl part containing 3 to 6 carbon atoms, unless indicated to the contrary and are optionally substituted, the alkylene radical designates the divalent $-(CH_2)_m-$ radical where m represents an integer equal to 1, 2, 3, 4, 5 or 6, the term "aryl" in "aryl" and "arylalkyl" signifies phenyl or naphthyl, optionally substituted, the term "heterocyclyl" in "heterocyclyl" and "heterocyclylalkyl" signifies a ring of 4 to 10 members, saturated, partially unsaturated or unsaturated, optionally substituted, comprising one or more heteroatoms, identical or different, chosen from nitrogen, oxygen, sulphur, silicon and phosphorus, when the amino radical is disubstituted, the two substituents are identical or different or may together with the nitrogen atom which carries them form a saturated, partially unsaturated or unsaturated nitrogen-containing heterocycle, containing 5 or 6 atoms in total, when the carbamoyl radical is disubstituted, the two substituents are identical or different or may together with the nitrogen atom which carries them form a saturated, partially unsaturated or unsaturated nitrogen-containing heterocycle of 5 to 6 carbon atoms in total, unless indicated to the contrary, the expression "optionally substituted" qualifying an organic group applies to different radicals constituting the group and indicates that the different radicals are optionally substituted by one or more radicals R9 and/or aryl and/or arylalkyl, identical or different.

According to one variant of the present invention, the invention relates to picolinic acid derivatives of general formula (I) as defined above and for which:

$X_1$ and $X_2$ each represent a hydrogen atom, the other substituents being as defined above, as well as the optional N-oxides, geometrical and/or optical isomers, enantiomers and/or diastereoisomers, tautomeric forms, salts and metal and metalloid complexes thereof, with the restriction that when $Q_1$ represents oxygen, G-Z represents a dialkylaminocarbonyloxy or dialkylaminothiocarbonyloxy radical, Y represents an $NH_2$ radical or an $N_3$ radical, $Q_2$ represents a radical $-NR_4R_5$ and $R_4$ represents an alkyl radical comprising from 1 to 12 carbon atoms, then $R_5$ cannot represent an alkyl radical comprising from 1 to 12 carbon atoms.

According to another variant of the present invention, this invention relates to picolinic acid derivatives of general formula (I) as defined above and for which:

$Q_1$ is chosen from an oxygen atom and a sulphur atom, the other substituents being as defined in claim 1, as well as the optional N-oxides, geometrical and/or optical isomers, enantiomers and/or diastereoisomers, tautomeric forms, salts and metal and metalloid complexes thereof, with the restriction that when $Q_1$ represents oxygen, G-Z represents a dialkylaminocarbonyloxy or dialkylaminothiocarbonyloxy radical, Y represents an $NH_2$ radical or an $N_3$ radical, $Q_2$ represents a radical $-NR_4R_5$ and $R_4$ represents an alkyl radical comprising from 1 to 12 carbon atoms, then $R_5$ cannot represent an alkyl radical comprising from 1 to 12 carbon atoms.

According to a third variant of the present invention, this invention relates to picolinic acid derivatives of general formula (I) as defined above and for which:

Z is chosen from an alkyl radical and a hydrogen atom or a cleavable radical capable of donating hydrogen, for example an alkoxyalkyl, haloalkoxyalkyl, alkylthioalkyl, haloalkylthioalkyl, N-alkylaminoalkyl, N,N-dialkylaminoalkyl, acylaminoalkyl, acyl, thioacyl, cyanoalkyl, alkoxythiocarbonyl, N-alkylaminothiocarbonyl, N,N-dialkylaminothiocarbonyl or alkylsulphinyl radical, the other substituents being as defined above, as well as the optional N-oxides, geometrical and/or optical isomers, enantiomers and/or diastereoisomers, tautomeric forms, salts and metal and metalloid complexes thereof, with the restriction that when $Q_1$ represents oxygen, G-Z represents a dialkylaminocarbonyloxy or dialkylaminothiocarbonyloxy radical, Y represents an $NH_2$ radical or an $N_3$ radical, $Q_2$ represents a radical $-NR_4R_5$ and $R_4$ represents an alkyl radical comprising from 1 to 12 carbon atoms, then $R_5$ cannot represent an alkyl radical comprising from 1 to 12 carbon atoms.

Another variant of the present invention relates to picolinic acid derivatives of general formula (I) as defined above and for which:

Y is chosen from a halogen atom, a hydroxyl, mercapto, nitro, thiocyanato, azido, cyano or pentafluorosulphonyl radical, an alkyl, haloalkyl, alkylthio, haloalkylthio, alkoxyalkyl, haloalkoxyalkyl, alkylthioalkyl, haloalkylthioalkyl, alkylsulphinyl, haloalkylsulphinyl, alkylsulphonyl, haloalkylsulphonyl or alkoxysulphonyl radical, an amino group, and an N-alkylamino, N,N-dialkylamino, $-NHCOR_{10}$, $-NHCSR_{10}$, N-arylamino, N,N-diarylamino, arylcarbonylamino, arylthiocarbonylamino, aryloxythiocarbonylamino or N,N-arylalkylaminothiocarbonylamino group, the other substituents being as defined above, as well as the optional N-oxides, geometrical and/or optical isomers, enantiomers and/or diastereoisomers, tautomeric forms, salts and metal and metalloid complexes thereof, with the restriction that when $Q_1$ represents oxygen, G-Z represents a dialkylaminocarbonyloxy or dialkylaminothiocarbonyloxy radical, Y represents an $NH_2$ radical or an $N_3$ radical, $Q_2$ represents a radical —$NR_4R_5$ and $R_4$ represents an alkyl radical comprising from 1 to 12 carbon atoms, then $R_5$ cannot represent an alkyl radical comprising from 1 to 12 carbon atoms.

According to yet another variant of the present invention, this invention relates to picolinic acid derivatives of general formula (I) as defined above and for which:

$Q_2$ represents a group —$NR_4R_5$, in which $R_4$ represents a hydrogen atom and $R_5$ is chosen from an optionally substituted alkyl radical comprising from 1 to 12 carbon atoms in a linear or branched chain, a haloalkyl, alkoxy, haloalkoxy, alkylthio, haloalkylthio, alkenyl or alkynyl radical and a radical chosen from aryl, arylalkyl, heterocyclyl and heterocyclylalkyl, optionally substituted with one or more radicals $R_9$ and/or aryl and/or arylalkyl, which may be identical or different, and/or a group -T-$R_8$, the other substituents being as defined above, as well as the optional N-oxides, geometrical and/or optical isomers, enantiomers and/or diastereoisomers, tautomeric forms, salts and metal and metalloid complexes thereof, with the restriction that when $Q_1$ represents oxygen, G-Z represents a dialkylaminocarbonyloxy or dialkylaminothiocarbonyloxy radical, Y represents an $NH_2$ radical or an $N_3$ radical, $Q_2$ represents a radical —$NR_4R_5$ and $R_4$ represents an alkyl radical comprising from 1 to 12 carbon atoms, then $R_5$ cannot represent an alkyl radical comprising from 1 to 12 carbon atoms.

More particularly, the present invention relates to picolinic acid derivatives of general formula (I) as defined above, which have the following characteristics, taken separately or in combination:

$X_1$ and $X_2$ each represent a hydrogen atom,

Z is chosen from an alkyl radical and a hydrogen atom or a cleavable radical capable of donating hydrogen, for example an alkoxyalkyl, haloalkoxyalkyl, alkylthioalkyl, haloalkylthioalkyl, N-alkylaminoalkyl, N,N-dialkylaminoalkyl, acylaminoalkyl, acyl, thioacyl, cyanoalkyl, alkoxythiocarbonyl, N-alkylaminothiocarbonyl, N,N-dialkylaminothiocarbonyl or alkylsulphinyl radical, Y is chosen from a halogen atom, a hydroxyl, mercapto, nitro, thiocyanato, azido, cyano or pentafluorosulphonyl radical, an alkyl, haloalkyl, alkylthio, haloalkylthio, alkoxyalkyl, haloalkoxyalkyl, alkylthioalkyl, haloalkylthioalkyl, alkylsulphinyl, haloalkylsulphinyl, alkylsulphonyl, haloalkylsulphonyl or alkoxysulphonyl radical, an amino group, and an N-alkylamino, N,N-dialkylamino, —$NHCOR_{10}$, —$NHCSR_{10}$, N-arylamino, N,N-diarylamino, arylcarbonylamino, arylthiocarbonylamino, aryloxythiocarbonylamino or N,N-arylalkylaminothiocarbonylamino group, $Q_1$ is chosen from an oxygen atom and a sulphur atom, $Q_2$ represents a group —$NR_4R_5$, in which $R_4$ represents a hydrogen atom and $R_5$ is chosen from an optionally substituted alkyl radical comprising from 1 to 12 carbon atoms in a linear or branched chain, a haloalkyl, alkoxy, haloalkoxy, alkylthio, haloalkylthio, alkenyl and alkynyl radical and a radical chosen from aryl, arylalkyl, heterocyclyl and heterocyclylalkyl, optionally substituted with one or more radicals $R_9$ and/or aryl and/or arylalkyl, which may be identical or different, and/or a group -T-$R_8$, the other substituents being as defined above, as well as the optional N-oxides, geometrical and/or optical isomers, enantiomers and/or diastereoisomers, tautomeric forms, salts and metal and metalloid complexes thereof, with the restriction that when $Q_1$ represents oxygen, G-Z represents a dialkylaminocarbonyloxy or dialkylaminothiocarbonyloxy radical, Y represents an $NH_2$ radical or an $N_3$ radical, $Q_2$ represents a radical —$NR_4R_5$ and $R_4$ represents an alkyl radical comprising from 1 to 12 carbon atoms, then $R_5$ cannot represent an alkyl radical comprising from 1 to 12 carbon atoms.

Even more particularly, the present invention relates to picolinic acid derivatives of general formula (I) as defined above, which have the following characteristics:

$X_1$ and $X_2$ each represent a hydrogen atom,

Z is chosen from an alkyl radical and a hydrogen atom or a cleavable radical capable of donating hydrogen, for example an alkoxyalkyl, haloalkoxyalkyl, alkylthioalkyl, haloalkylthioalkyl, N-alkylaminoalkyl, N,N-dialkylaminoalkyl, acylaminoalkyl, acyl, thioacyl, cyanoalkyl, alkoxythiocarbonyl, N-alkylaminothiocarbonyl, N,N-dialkylaminothiocarbonyl or alkylsulphinyl radical, Y is chosen from a halogen atom, a hydroxyl, mercapto, nitro, thiocyanato, azido, cyano or pentafluorosulphonyl radical, an alkyl, haloalkyl, alkylthio, haloalkylthio, alkoxyalkyl, haloalkoxyalkyl, alkylthioalkyl, haloalkylthioalkyl, alkylsulphinyl, haloalkylsulphinyl, alkylsulphonyl, haloalkylsulphonyl or alkoxysulphonyl radical, an amino group, and an N-alkylamino, N,N-dialkylamino, —$NHCOR_{10}$, —$NHCSR_{10}$, N-arylamino, N,N-diarylamino, arylcarbonylamino, arylthiocarbonylamino, aryloxythiocarbonylamino or N,N-arylalkylaminothiocarbonylamino group, $Q_1$ is chosen from an oxygen atom and a sulphur atom, $Q_2$ represents a group —$NR_4R_5$, in which $R_4$ represents a hydrogen atom and $R_5$ is chosen from an optionally substituted alkyl radical comprising from 1 to 12 carbon atoms in a linear or branched chain, a haloalkyl, alkoxy, haloalkoxy, alkylthio, haloalkylthio, alkenyl and alkynyl radical and a radical chosen from aryl, arylalkyl, heterocyclyl and heterocyclylalkyl, optionally substituted with one or more radicals $R_9$ and/or aryl and/or arylalkyl, which may be identical or different, and/or a group -T-$R_8$, the other substituents being as defined above, as well as the optional N-oxides, geometrical and/or optical isomers, enantiomers and/or diastereoisomers, tautomeric forms, salts and metal and metalloid complexes thereof, with the restriction that when $Q_1$ represents oxygen, G-Z represents a dialkylaminocarbonyloxy or dialkylaminothiocarbonyloxy radical, Y represents an $NH_2$ radical or an $N_3$ radical, $Q_2$ represents a radical —$NR_4R_5$ and $R_4$ represents an alkyl radical comprising from 1 to 12 carbon atoms, then $R_5$ cannot represent an alkyl radical comprising from 1 to 12 carbon atoms.

Even more specifically, the present invention relates to picolinic acid derivatives of general formula (I) as defined above, which have the following characteristics:

$X_1$ and $X_2$ each represent a hydrogen atom,

Z is chosen from an alkyl radical and a hydrogen atom or a cleavable radical capable of donating hydrogen, for example an alkoxyalkyl, haloalkoxyalkyl, alkylthioalkyl, haloalkylthioalkyl, N-alkylaminoalkyl, N,N-dialkylaminoalkyl, acylaminoalkyl, acyl, thioacyl, cyanoalkyl, alkoxythiocarbonyl, N-alkylaminothiocarbonyl, N,N-dialkylaminothiocarbonyl or alkylsulphinyl radical, Y is chosen from a halogen atom, a hydroxyl, azido, alkylthio and alkylsulphonyl radical and an amino, —$NHCOR_{10}$ and —$NHCSR_{10}$ group, $Q_1$ represents an oxygen atom, $Q_2$ represents a group —$NR_4R_5$, in which $R_4$ represents a hydrogen atom and $R_5$ is chosen from an aryl, arylalkyl, heterocyclyl and heterocyclylalkyl radical, optionally substituted with one or more radicals $R_9$ and/or aryl and/or arylalkyl, which may be identical or different, and/or a group -T-$R_8$, the other substituents being as defined above, as well as the optional N-oxides, geometrical and/or optical isomers, enantiomers and/or diastereoisomers, tautomeric forms, salts and metal and metalloid complexes thereof.

In the context of the present invention, the term "aryl" means phenyl or naphthyl, the term "arylalkyl" means phenylalkyl or naphthylalkyl, more particularly benzyl, phenethyl, phenylpropyl, phenylbutyl, naphthylmethyl, naphthylethyl, naphthylpropyl or naphthylbutyl. It is understood that these various radicals may optionally be substituted with one or more radicals $R_9$ and/or aryl and/or arylalkyl radicals, which may be identical or different.

The terms "heterocyclyl" and "heterocyclylalkyl" are defined similarly, it being understood that "heterocycle" means a saturated, partially unsaturated or unsaturated monocycle or bicycle containing from 4 to 10 ring units, comprising at least one hetero atom chosen from nitrogen, oxygen, sulphur, silicon and phosphorus.

More particularly, the term "heterocycle" is understood as being one of the rings (i) to (v) below:

a 5-membered ring described by formula (i):

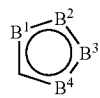

(i)

in which each of the groups of the list $B^1$, $B^2$, $B^3$ $B^4$ is chosen from carbon, nitrogen, oxygen and sulphur atoms such that the said list comprises from 0 to 3 carbon atoms, from 0 to 1 sulphur atom, from 0 to 1 oxygen atom and from 0 to 4 nitrogen atoms;

a 6-membered ring described by formula (ii):

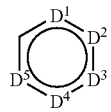

(ii)

in which each of the groups of the list $D^1$, $D^2$, $D^3$, $D^4$, $D^5$ is chosen from carbon and nitrogen atoms such that the said list comprises from 1 to 4 carbon atoms and from 1 to 4 nitrogen atoms; two fused rings, each being 6-membered, described by formula (iii):

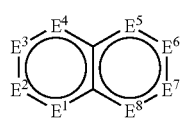

(iii)

in which each of the groups in the list $E^1$, $E^2$, $E^3$, $E^4$, $E^5$, $E^6$, $E^7$, $E^8$ is chosen from carbon and nitrogen atoms such that the said list comprises from 4 to 7 carbon atoms and from 1 to 4 nitrogen atoms;

a 6-membered ring and a 5-membered ring fused together, described by formula (iv):

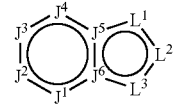

(iv)

in which:

each of the groups in the list $J^1$, $J^2$, $J^3$, $J^4$, $J^5$, $J^6$ is chosen from carbon and nitrogen atoms such that the said list comprises from 3 to 6 carbon atoms and from 0 to 3 nitrogen atoms; and each of the groups in the list L1, L2, L3 is chosen from carbon, nitrogen, oxygen and sulphur atoms such that the said list comprises from 0 to 3 carbon atoms, from 0 to 1 sulphur atom, from 0 to 1 oxygen atom and from 0 to 3 nitrogen atoms; and each of the groups in the list $J^1$, $J^2$, $J^3$, $J^4$, $J^5$, $J^6$, $L^1$, $L^2$, $L^3$ is chosen such that the said list comprises from 3 to 8 carbon atoms;

two fused rings, each being 5-membered, described by formula (v):

(v)

in which:

each of the groups in the list $M^1$, $M^2$, $M^3$ represents, carbon, nitrogen, oxygen or sulphur atoms such that the said list comprises from 0 to 3 carbon atoms, from 0 to 1 sulphur atom, from 0 to 1 oxygen atom and from 0 to 3 nitrogen atoms;

each of the groups in the list $T^1$, $T^2$, $T^3$ represents carbon, nitrogen, oxygen or sulphur atoms such that the said list comprises from 0 to 3 carbon atoms, from 0 to 1 sulphur atom, from 0 to 1 oxygen atom and from 0 to 3 nitrogen atoms; $Z^1$ represents a carbon or nitrogen atom;

each of the groups in the list $M^1$, $M^2$, $M^3$, $T^1$, $T^2$, $T^3$ is chosen such that the said list comprises from 0 to 6 carbon atoms.

In the present invention, the term "heterocycle" even more particularly means: furyl, pyrolyl, thienyl, pyrazolyl, imidazolyl, oxazolyl, isoxazolyl, thiazolyl, isothiazolyl, 1,2,3-oxadiazolyl, 1,2,4-oxadiazolyl, 1,2,5-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, 1,2,3-triazolyl, 1,2,4-triazolyl, tetrazolyl, pyridyl, pyrimidinyl, pyrazinyl, pyridazinyl, 1,2,3-triazinyl, 1,2,4-triazinyl, 1,3,5-triazinyl, 1,2,3,4-tetrazinyl, 1,2,3,5-tetrazinyl, 1,2,4,5-tetrazinyl, benzimidazolyl, indazolyl, benzotriazolyl, benzoxazolyl, 1,2-benzisoxazolyl, 2,1-benzisoxazolyl, benzothiazolyl, 1,2-benzisothiazolyl, 2,1-benzisothiazolyl, 1,2,3-benzoxadiazolyl, 1,2,5-benzoxadiazolyl, 1,2,3-benzothiadiazolyl, 1,2,5-benzothiadiazolyl, quinolyl, isoquinolyl, quinoxazolinyl, quinazolinyl, cinnolyl or phthalazyl, pteridinyl, benzotriazinyl, 1,5-naphthyridinyl, 1,6-naphthyridinyl, 1,7-naphthyridinyl, 1,8-naphthyridinyl, imidazo[2,1-b]thiazolyl, thieno[3,4-b]pyridyl, purine or pyrrolo[1,2-b]thiazolyl.

The present invention most particularly relates to picolinic acid derivatives of general formula (I) as defined above, which are:

4-amino-3-hydroxy-N-[4-(4-methylphenoxy)phenyl]-2-pyridinecarboxamide,
4-(formylamino)-3-hydroxy-N-{4-[3-(trifluoromethyl)phenoxy]phenyl}-2-pyridinecarboxamide,
4-amino-3-hydroxy-N-{4-[4-(trifluoromethyl)phenoxy]phenyl}-2-pyridinecarboxamide,
N-[4-(4-chlorophenoxy)phenyl]-4-(formylamino)-3-hydroxy-2-pyridinecarboxamide,
4-(formylamino)-3-hydroxy-N-{4-[4-(trifluoromethyl)phenoxy]phenyl}-2-pyridinecarboxamide and
N-[4-(benzyloxy)phenyl]-4-(formylamino)-3-hydroxy-2-pyridinecarboxamide, as well as the optional N-oxides, geometrical and/or optical isomers, enantiomers and/or diastereoisomers, tautomeric forms, salts and metal and metalloid complexes thereof.

The compounds of general formula (I) and the compounds which may be used as intermediates in the processes of preparation, and which will be defined in the description of these processes, can exist in one or more forms of geometrical isomers according to the number of double bonds in the compound. The compounds of general formula (I) where $Q_1$ is $-NR_1$ or $-N-NR_4R_5$ can comprise 2 different geometrical isomers denoted (E) or (Z) depending on the configuration of the two double bonds. The E and Z notation can be replaced, respectively, by the term "syn" and "anti", or "cis" and "trans". Reference is made particularly to the work of E. Eliel and S. Wilen "Stereochemistry of Organic Compounds", published by Wiley (1994), for the description and use of these notations.

The compounds of general formula (I) and compounds which may be used as intermediates in the processes of preparation, and which will be defined in the description of the processes, can exist in one or more optical isomeric or chiral forms according to the number of asymmetric centres in the compound. The invention thus also relates to all the optical isomers and their racemic or scalemic (scalemic designates a mixture of enantiomers in different proportions), as well as the mixtures of all possible stereoisomers in all proportions, including the racemic mixture. The separation of the diastereoisomers and/or optical isomers can be effected by known methods (E. Eliel ibid.).

The present invention also relates to the process of preparation of the compounds of general formula (I) and compounds useful as intermediates in the processes of preparation. The compounds can be prepared according to the general method of preparation described below. Although general, this method of preparation provides all of the operating conditions to be used for the synthesis of the compounds of formula (I) according to the present invention. It will nevertheless be understood that the skilled worker will be able to adapt this method according to the specifics of each of the compounds which it is desired to synthesise.

The preparation of reagents used in one or other of the general methods of preparation is generally known and is generally described specifically in the prior art or in such a manner that the man skilled in the art can adapt it to the desired aim. The prior art usable by the normally skilled worker in order to establish conditions for the preparation of reagents can be found in numerous general chemistry text books such as "Advanced Organic Chemistry" by J. March, published by Wiley (1992), "Methoden der organischen Chemie" (Houben-Weyl), published by Georg Thieme Verlag or the "Chemical Abstracts" published by the American Chemical Society as well as in information data bases accessible to the public.

The compounds of general formula (I), in which G represents oxygen, Z represents hydrogen and n is equal to 0, may be prepared from a compound of formula (IIa) (prepared, for example, according to the method described in the publication by R. H. Dodd, Heterocycles, 47, (1998), 811):

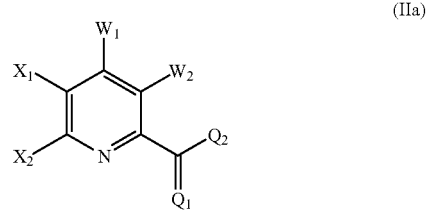

(IIa)

in which $Xl_1$, $X_2$, $Q_1$ and $Q_2$ are as defined above and $W_1$ and $W_2$, which may be identical or different, represent, independently of each other, a halogen atom chosen from fluorine, chlorine, bromine and iodine, which is placed in contact with an azothydric acid salt, more particularly, but not exclusively, sodium azide, this reaction preferably being carried out in a polar aprotic solvent such as dimethylformamide, dimethylacetamide, N-methylpyrrolidone, dimethylpropylene urea or dimethyl sulphoxide, at reflux or at a temperature of between 20° C. and 200° C., to give the compounds of formula (IIIa):

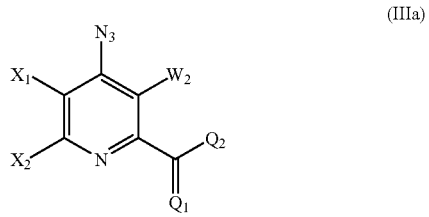

(IIIa)

in which $X_1$, $X_2$, $Q_1$ and $Q_2$ are as defined above and $W_2$ represents a halogen atom chosen from fluorine, chlorine, bromine and iodine.

The azides of formula (IIIa) above are then optionally reduced to the corresponding amine derivatives of formula (IVa):

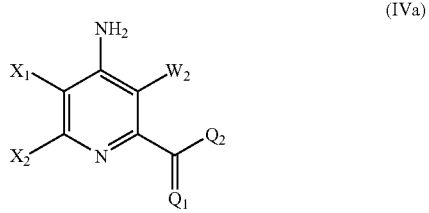

(IVa)

in which $X_1$, $X_2$, $Q_1$, and $Q_2$ are as defined above and $W_2$ represents a halogen atom chosen from fluorine, chlorine, bromine and iodine, by the action of a reducing agent such as, for example, triphenylphosphine, sodium borohydride or hydrogen in the presence of a catalyst, or alternatively as described by J. March, ibid, pages 1219-1220.

The compounds of formula (IVa) may then be hydrolyzed to 3-hydroxypicolinic derivatives of formula (Va):

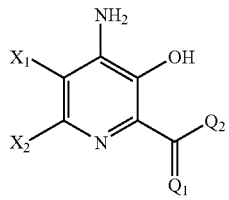

(Va)

in which $X_1$, $X_2$, $Q_1$ and $Q_2$ are as defined above, by the action of an inorganic base such as, but not exclusively, alkali metal hydroxides and alkaline-earth metal hydroxides such as sodium hydroxide, potassium hydroxide, cesium hydroxide or calcium hydroxide. This reaction is generally carried out at a temperature of between 0° C. and the boiling point of the solvent, in a polar aprotic dipolar solvent such as dimethylformamide, dimethylacetamide, N-methylpyrrolidone, dimethylpropyleneurea, dimethyl sulphoxide or water.

The compounds of formula (Va) may optionally be subjected to various alkylation reactions that are well known to those skilled in the art, so as to give the compounds of formula (VIa):

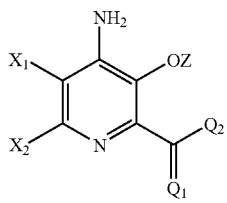

(VIa)

in which $X_1$, $X_2$, Z, $Q_1$ and $Q_2$ are as defined above.

The compounds of general formula (I) in which G represents sulphur may also be advantageously prepared from a compound of formula (IIb) (prepared, for example, according to the method described in the publication by R. H. Dodd, *Heterocycles*, 47, (1998), page 811):

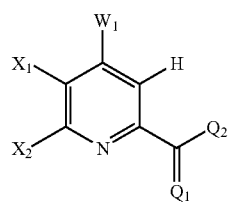

(IIb)

in which $X_1$, $X_2$, $Q_1$ and $Q_2$ are as defined above and $W_1$ represents a halogen atom chosen from fluorine, chlorine, bromine and iodine, by reaction of an organic base such as, but not exclusively, lithium diisopropylamide, and sulphur, to give the compounds of formula (IIIb):

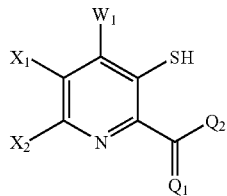

(IIIb)

in which $Xl_1$, $X_2$, $W_1$, $Q_1$, and $Q_2$ are as defined above.

The solvent which is suitable for this reaction may be an aliphatic hydrocarbon such as pentane, hexane, heptane or octane; an aromatic hydrocarbon such as benzene or toluene; an ether such as diethyl ether, diisopropyl ether or tetrahydrofuran. The reaction is generally carried out at a temperature of between −100° C. and 0° C.

The thiols of formula (IIIb) may then be converted into compounds of formula (IVb):

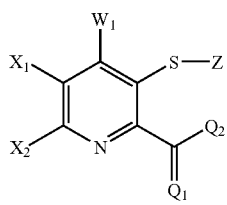

(IVb)

in which $X_1$, $X_2$, $W_1$, $Q_1$ and $Q_2$ are as defined above, by reaction with an alkylating agent such as, but not exclusively, methyl iodide or 4-methoxybenzyl chloride.

This reaction requires the presence of an organic or inorganic base, such as sodium hydroxide, potassium hydroxide, cesium hydroxide or calcium hydroxide, alkali metal alkoxides such as potassium tert-butoxide, alkali metal hydrides and alkaline-earth metal hydrides, such as sodium hydride, potassium hydride or cesium hydride, alkali metal and alkaline-earth metal carbonates and bicarbonates, such as sodium carbonate, potassium carbonate or calcium carbonate, organic bases, preferably organonitrogen bases, such as pyridine, alkylpyridines, alkylamines such as trimethylamine, triethylamine or diisopropylethylamine, aza derivatives such as 1,5-diazabicyclo[4.3.0]non-5-ene or 1,8-diazabicyclo[5.4.0]undec-7-ene. The reaction is generally carried out at a temperature of between −80° C. and 180° C. (preferably between 0° C. and 150° C.) or at the boiling point of the solvent used. The solvent which is suitable for this reaction may be an aliphatic hydrocarbon such as pentane, hexane, heptane or octane; an aromatic hydrocarbon such as benzene, toluene or xylenes; an ether such as diethyl ether, diisopropyl ether, tetrahydrofuran, dioxane or dimethoxyethane; a halogenated hydrocarbon such as dichloromethane, chloroform or 1,2-dichloroethane; a nitrile such as acetonitrile, propionitrile or benzonitrile; an aprotic dipolar solvent such as dimethylformamide, dimethylacetamide, N-methylpyrrolidone, dimethylpropyleneurea, dimethyl sulphoxide or water.

The compounds of formula (IVb) may then be converted into 4-amino compounds of formula (Vb):

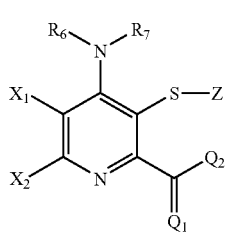

(Vb)

in which $X_1$, $X_2$, $Q_1$, $Q_2$, Z, $R_6$ and $R_7$ are as defined above,
by reacting a compound of formula $R_6R_7NH$, or a corresponding alkali metal or alkaline-earth metal salt, in the absence of solvent or in a polar aprotic solvent, such as dimethylformamide, dimethylacetamide, N-methylpyrrolidine, dimethylpropyleneurea or dimethyl sulphoxide, at a temperature of between 0° C. and the boiling point of the solvent.

The compounds of formula (Vb) in which $X_1$, $X_2$, $Q_1$, $Q_2$, $R_6$ and $R_7$ are as defined above and Z represents a 4-methoxybenzilic group may be converted into the corresponding 3-thiopyridine by reaction with an organic acid such as, but not exclusively, trifluoroacetic acid, this reaction preferably being carried out in a polar protic solvent, for instance alcohols such as ethanol, methanol, propanol or cresol,
at reflux or at a temperature of between 20 C. and 200° C., to give the compounds of formula (VIb):

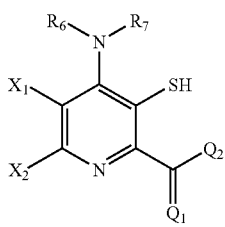

(VIb)

in which $X_1$, $X_2$, $Q_1$, $Q_2$, $R_6$ and $R_7$ are as defined above.

The compounds of formula (IVb) may also be converted into azides of formula (VIIb):

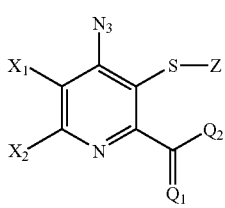

(VIIb)

in which $X_1$, $X_2$, $Q_1$, $Q_2$ and Z are as defined above,
by reaction with an azothydric acid salt, more particularly, but not exclusively, sodium azide, preferably in a polar aprotic solvent such as dimethylformamide, dimethylacetamide, N-methylpyrrolidone, dimethylpropyleneurea or dimethyl sulphoxide, at reflux or at a temperature between 20° C. and 200° C.

The compounds of formula (VIIb) may then be hydrolysed to compounds of formula (VIIIb):

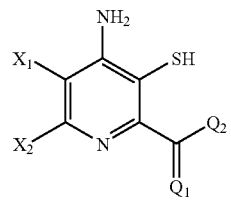

(VIIIb)

in which $X_1$, $X_2$, $Q_1$ and $Q_2$ are as defined above,
by the action of a reducing agent such as, for example, triphenylphosphine or hydrogen, in the presence of a catalyst, or alternatively as described by J. March, ibid., pages 1219-1220.

The compounds of formulae (Va), (VIa) and (VIIIb) defined above may optionally be placed in contact with an acylating agent in the presence of a solvent and optionally of a base. The term "acylating agent" preferably means, but not in a limiting manner, an acyl halide, an anhydride, an acid, an ester, a primary amide and thio homologues thereof, as described in J. March, ibid., pages 417-424, to give the compounds of formulae ($IX_1$) and ($IX_2$):

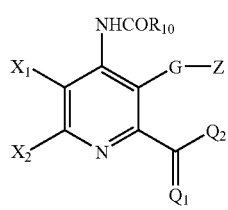

($IX_1$)

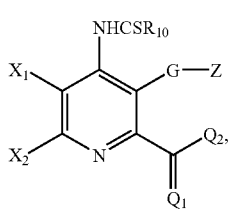

($IX_2$)

in which G, $X_1$, $X_2$, $Q_1$, $Q_2$ Z and $R_{10}$ are as defined above.

The compounds of formulae (VIa) and (IVb) may also optionally be subjected to various substitution and/or addition reactions that are well known to those skilled in the art to give the set of compounds of formula (X):

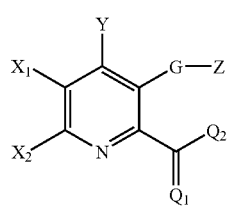

(X)

in which G, $X_1$, $X_2$, $Q_1$, $Q_2$, Y and Z are as defined above, which is a special case of the compounds of formula (I) for which n represents zero.

The compounds of general formula (XI):

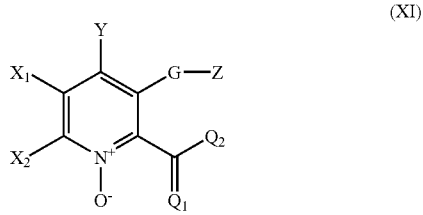

which are special cases of the compounds of formula (I) for which n is equal to 1,
may be obtained by a process which consists in placing a compound of formula (X), which is a special case of the compounds of formula (I) for which n is equal to zero,
in contact with an oxidizing agent as described in J. March, ibid., page 1200, in particular aqueous hydrogen peroxide solution or carboxylic, boronic or sulphuric peracids.

It should be understood that the reactions described in the preceding paragraphs may be carried out in any other order which is suitable to obtain the desired compounds of formula (I). The order of the reactions will be determined most particularly by the compatibility requirements of the various substituents on the pyridine nucleus. The compatibilities of the various radicals and reagents used are well known to the person skilled in the art, who may moreover refer to the examples for the preparation of the compounds of formula (I) described later in this description.

The invention also relates to fungicidal compositions comprising an effective amount of at least one active material of formula (I). The fungicidal compositions according to the invention comprise, besides the active material of formula (I), agriculturally acceptable solid or liquid supports and/or surfactants which are also agriculturally acceptable. In particular, common inert supports and common surfactants can be used. These compositions include not only compositions which are ready to be applied to the plant or seed to be treated by means of a suitable device, such as a spraying or dusting device, but also concentrated commercial compositions which must be diluted before they are applied to the crop.

These fungicidal compositions according to the invention can also contain other ingredients of any kind, such as, for example, protective colloids, adhesives, thickeners, thixotropic agents, penetration agents, stabilizers, sequestering agents, etc. More generally, the active materials can be combined with any solid or liquid additive which complies with the usual formulation techniques.

In general, the compositions according to the invention usually contain from 0.05 to 99% (by weight) of active material, one or more solid or liquid supports and, optionally, one or more surfactants.

In the present specification, the term "support" denotes a natural or synthetic, organic or inorganic material with which the active material is combined to make it easier to apply to the parts of the plant. This support is thus generally inert and should be agriculturally acceptable. The support can be solid (clays, natural or synthetic silicates, silica, resins, waxes, solid fertilizers, etc.) or liquid (water, alcohols, in particular butanol, etc., organic solvents, mineral and plant oils and derivatives thereof). Mixtures of such supports may also be used.

The surfactant can be an emulsifier, a dispersing agent or a wetting agent of ionic or nonionic type or a mixture of such surfactants. Mention may be made, for example, of polyacrylic acid salts, lignosulphonic acid salts, phenolsulphonic or naphthalenesulphonic acid salts, polycondensates of ethylene oxide with fatty alcohols or with fatty acids or with fatty amines, substituted phenols (in particular alkylphenols or arylphenols), salts of sulphosuccinic acid esters, taurine derivatives (in particular alkyl taurates), phosphoric esters of polyoxyethylated alcohols or phenols, fatty acid esters of polyols, and derivatives of the above compounds containing sulphate, sulphonate and phosphate functions. The presence of at least one surfactant is generally essential when the active material and/or the inert support are water-insoluble and when the vector agent for the application is water.

Thus, the compositions for agricultural use according to the invention can contain the active material in a very wide range, from 0.05% to 99% (by weight). Their surfactant content is advantageously between 5% and 40% by weight. Except where otherwise indicated, the percentages given in this description are weight percentages.

These compositions according to the invention are themselves in quite diverse, solid or liquid forms. As solid composition forms, mention may be made of powders for dusting (with an active material content which can be up to 100%) and granules, in particular those obtained by extrusion, by atomization, by compacting, by impregnation of a granulated support or by granulation from a powder (the active material content in these granules being between 0.5 and 80% for the latter cases).

The fungicidal compositions according to the invention can also be used in the form of powders for dusting; compositions comprising 50 g of active material and 950 g of talc can also be used; compositions comprising 20 g of active material, 10 g of finely divided silica and 970 g of talc can also be used; these constituents are mixed together and ground and the mixture is applied by dusting.

As liquid composition forms or forms intended to constitute liquid compositions when applied, mention may be made of solutions, in particular water-soluble concentrates, emulsifiable concentrates, emulsions, concentrated suspensions and wettable powders (or powders for spraying).

The concentrated suspensions, which can be applied by spraying, are prepared so as to obtain a stable fluid product which does not become deposited and which gives good bioavailability of the active material(s). These suspensions usually contain from 5% to 75% of active material, preferably from 10% to 25%, from 0.5% to 75% of surfactants, preferably from 5% to 50%, from 0% to 10% of suitable additives, such as thickeners of organic or mineral origin, antifoaming agents, corrosion inhibitors, adhesives, preserving agents, such as, for example, Proxel GXL®, antifreezes and, as support, water or an organic liquid in which the active material is insoluble or only sparingly soluble: certain organic solid materials or mineral salts may be dissolved in the support to help prevent sedimentation or as antifreezes for the water. In certain cases, and in particular for formulations intended for treating seeds, one or more colorants may be added.

For foliar applications, the choice of surfactants is paramount for obtaining good bioavailability of the active material(s); thus, a combination of a surfactant of hydrophilic nature (HLB>10) and a surfactant of lipophilic nature (HLB<5) will preferably be used. Such combinations of surfactants are disclosed, for example, in the as yet unpublished French patent No. 00/04015.

By way of example, here are 3 possible formulations of concentrated suspension type that are suitable for various crops:

EXAMPLE CS 1 (in k/kg)

This example is rather suited for monocotyledon crops (cereals, rice, etc.)

| | |
|---|---|
| active material | 150 |
| surfactant of hydrophilic nature (for example Rhodasurf 860P) | 300 |
| surfactant of lipophilic nature (for example Plurafac LF 700) | 150 |
| ethoxylated tristyrylphenol phosphate | 50 |
| antifoam | 5 |
| propylene glycol | 30 |
| Aerosil 200 | 20 |
| Attagel 50 | 40 |
| water (qs 1 kg) | 255 |

EXAMPLE CS 2 (in g/kg)

This example is suited rather to dicotyledon crops (vines, fruit trees, etc.)

| | |
|---|---|
| active material | 150 |
| surfactant of hydrophilic nature (for example Rhodasurf 860P) | 150 |
| ethoxylated tristyrylphenol phosphate | 50 |
| antifoam | 5 |
| propylene glycol | 30 |
| Aerosil 200 | 20 |
| Attagel 50 | 40 |
| water (qs 1 kg) | 555 |

EXAMPLE CS 3 (in k/kg)

This example is more specifically suited to the treatment of seeds.

| | |
|---|---|
| active material | 50 |
| surfactant of hydrophilic nature (for example Rhodasurf 860P) | 5 |
| ethoxylated tristyrylphenol phosphate | 15 |
| antifoam | 1 |
| propylene glycol | 30 |
| colorant | 20 |
| Rhodopol G | 1.5 |
| Proxel GXL | 1.5 |
| water (qs 1 kg) | 876 |

The following procedure will preferably be carried out to prepare these formulations: The surfactants selected (surfactant of hydrophilic nature+surfactant of lipophilic nature+ethoxylated tristyrylphenol phosphate) are mixed with the required amount of water, using a turbo mixer; after homogenization, the other constituents of the formulation apart from the active material are then mixed together.

Next, the active material and optionally the thickener of mineral origin (Aerosol 200 and Attagel 50) are added to give a medium of viscous consistency.

The mixture obtained is then ground using a turbo mixer mill at high speed and then a ball mill until a D50 of about 1 to 3 µm and a D90 of between 3 and 8 µm are obtained.

When no thickener of mineral origin is used, the thickener of natural origin (Rhodopol G) is then added and the mixture is stirred until a suitable viscosity is obtained.

The wettable powders (or powders for spraying) are usually prepared such that they contain 20 to 95% of active material, and they usually contain, in addition to the solid support, from 0 to 30% of a wetting agent, from 3 to 20% of a dispersant and, when necessary, from 0.1 to 10% of one or more stabilizers and/or other additives, such as penetration agents, adhesives, anticaking agents, dyes, etc.

In order to obtain the powders for spraying or wettable powders, the active materials are intimately mixed with the additional substances in suitable mixers and are ground with mills or other suitable blenders. Powders for spraying with advantageous wettability and suspension formation are thus obtained; they can be placed in suspension with water at any desired concentration and these suspensions can be used very advantageously, in particular for application, for example, to plant leaves or to seeds.

By way of example, there follow various wettable powder compositions (or powders for spraying):

EXAMPLE WP1

| | |
|---|---|
| Active material | 50% |
| Ethoxylated fatty alcohol (wetting agent) | 2.5% |
| Ethoxylated phenylethylphenol (dispersant) | 5% |
| Chalk (inert support) | 42.5% |

EXAMPLE WP2

| | |
|---|---|
| Active material | 10% |
| Synthetic C13 oxo alcohol of branched type, ethoxylated with 8 to 10 ethylene oxide (wetting agent) | 0.75% |
| Neutral calcium lignosulphonate (dispersant) | 12% |
| Calcium carbonate (inert filler) | qs 100% |

EXAMPLE WP3

This wettable powder contains the same ingredients as in the above example, in the following proportions:

| | |
|---|---|
| Active material | 75% |
| Wetting agent | 1.50% |
| Dispersant | 8% |
| Calcium carbonate (inert filler) | qs 100% |

EXAMPLE WP4

| | |
|---|---|
| Active material | 90% |
| Ethoxylated fatty alcohol (wetting agent) | 4% |
| Ethoxylated phenylethylphenol (dispersant) | 6% |

EXAMPLE WP5

| Active material | 50% |
| --- | --- |
| Mixture of anionic and nonionic surfactants (wetting agent) | 2.5% |
| Sodium lignosulphonate (dispersant) | 5% |
| Kaolinic clay (inert support) | 42.5% |

The aqueous dispersions and emulsions, for example the compositions obtained by diluting a wettable powder according to the invention with water, are included within the general scope of the present invention. The emulsions can be of the water-in-oil or oil-in-water type and they can have a thick consistency, such as that of a "mayonnaise".

The fungicidal compositions according to the invention can be formulated in the form of water-dispersible granules, which are also included within the scope of the invention. These dispersible granules, with an apparent density generally of between about 0.3 and about 0.6, have a particle size generally of between about 150 and about 2000 and preferably between 300 and 1500 microns.

The active material content of these granules is generally between about 1% and about 90% and preferably between 25% and 90%. The rest of the granule is essentially composed of a solid support and optionally of surfactant adjuvants which give the granule water-dispersibility properties. These granules can be essentially of two different types depending on whether the support selected is soluble or insoluble in water. When the support is water-soluble, it can be inorganic or, preferably, organic. Excellent results have been obtained with urea. In the case of an insoluble support, it is preferably inorganic, for example such as kaolin or bentonite. It is then advantageously accompanied by surfactants (in a proportion of from 2 to 20% by weight of the granule) more than half of which consists, for example, of at least one dispersant, which is essentially anionic, such as an alkali metal or alkaline-earth metal polynaphthalene sulphonate or an alkali metal or alkaline-earth metal lignosulphonate, the remainder consisting of nonionic or anionic wetting agents such as an alkali metal or alkaline-earth metal alkylnaphthalene sulphonate. Moreover, although this is not essential, other adjuvants can be added, such as antifoaming agents.

The granule according to the invention can be prepared by mixing together the required ingredients, followed by granulation according to several techniques which are known per se (granulator, fluid bed, sprayer, extrusion, etc.). The process generally ends by a crushing operation, followed by an operation of screening to the particle size chosen within the limits mentioned above. Granules obtained as above and then impregnated with a composition containing the active material can also be used.

Preferably, it is obtained by extrusion, by performing the process as indicated in the examples below.

EXAMPLE DG1

Dispersible Granules

90% by weight of active material and 10% of urea pellets are mixed together in a mixer. The mixture is then ground in a toothed roll crusher. A powder is obtained, which is moistened with about 8% by weight of water. The wet powder is extruded in a perforated-roller extruder. A granulate is obtained, which is dried and then crushed and screened, so as to retain, respectively, only the granules between 150 and 2000 microns in size.

EXAMPLE DG2

Dispersible Granules

The constituents below are mixed together in a mixer:

| Active material | 75% |
| --- | --- |
| Wetting agent (sodium alkylnaphthalene sulphonate) | 2% |
| Dispersant (polysodium naphthalene sulphonate) | 8% |
| Water-insoluble inert filler (kaolin) | 15% |

This mixture is granulated in a fluid bed, in the presence of water, and then dried, crushed and screened so as to obtain granules between 0.15 and 0.80 mm in size.

These granules can be used alone, or as a solution or dispersion in water so as to obtain the desired dose. They can also be used to prepare combinations with other active materials, in particular fungicides, these being in the form of wettable powders, granules or aqueous suspensions.

The compounds of the invention can also be mixed with one or more insecticides, fungicides, bactericides, attractant acaricides or pheromones or other compounds with biological activity. The mixtures thus obtained have a broadened spectrum of activity. In particular the compounds of the present invention do not exhibit the problem of cross-resistance with strobilurin derivatives. In fact the compounds of the present invention are active on a different biochemical site to strobilurin derivatives.

The mixtures with other fungicides are particularly advantageous, especially the mixtures with acibenzolar-S-methyl, azoxystrobin, benalaxyl, benomyl, blasticidin-S, bromuconazole, captafol, captan, carbendazim, carboxin, carpropamide, chlorothalonil, fungicidal compositions based on copper, derivatives of copper such as copper hydroxide and copper oxychloride, cyazofamide, cymoxanil, cyproconazole, cyprodinil, dichloran, diclocymet, diethofencarb, difenoconazole, diflumetorim, dimethomorph, diniconazole, discostrobin, dodemorph, dodine, edifenphos, epoxyconazole, ethaboxam, ethirimol, famoxadone, fenamidone, fenarimol, fenbuconazole, fenhexamide, fenpiclonil, fenpropidine, fenpropimorph, ferimzone, fluazinam, fludioxonil, flumetover, fluquinconazole, flusilazole, flusulfamide, flutolanil, flutriafol, folpel, furalaxyl, furametpyr, guazatine, hexaconazole, hymexazol, imazalil, iprobenphos, iprodione, isoprothiolane, kasugamycin, kresoxim-methyl, mancozeb, maneb, mefenoxam, mepanipyrim, metalaxyl and their enantiomeric forms such as metalaxyl-M, metconazole, metiramzinc, metominostrobin, oxadixyl, pefurazoate, penconazole, pencycuron, phosphorous acid and its derivatives such as fosetyl-Al, phtalide, picoxystrobin, probenazole, prochloraz, procymidone, propamocarb, propiconazole, pyraclostrobin, pyrimethanil, pyroquilon, quinoxyfen, silthiofam, simeconazole, spiroxamine, tebuconazole, tetraconazole, thiabendazole, thifluzamide, thiophanate, for example thiophanate-methyl, thiram, triadimefon, triadimenol, tricyclazole, tridemorph, trifloxystrobin, triticonazole, derivatives of valinamide such as for example, iprovalicarb, vinclozolin, zineb and zoxamide.

Another subject of the invention is a process for curatively or preventively combating the phytopathogenic fungi of crops, characterized in that an effective (agronomically effective) and non-phytotoxic amount of an active material of formula (I), preferably in the form of a fungicidal composition according to the invention, is applied to the plant seeds or to the plant leaves and/or to the fruits of the plants or to the soil in which the plants are growing or in which it is desired to grow them.

The expression "effective and non-phytotoxic amount" means an amount of composition according to the invention which is sufficient to control or destroy the fungi present or liable to appear on the crops, and which does not entail any appreciable symptom of phytotoxicity for the said crops. Such an amount can vary within a wide range depending on the fungus to be combated, the type of crop, the climatic conditions and the compounds included in the fungicidal composition according to the invention. This amount can be determined by systematic field trials, which are within the capabilities of a person skilled in the art.

Lastly, the invention relates to a process for preventively or curatively protecting plant multiplication products, as well as the plants resulting therefrom, against fungal diseases, characterized in that the said products are coated with an effective and non-phytotoxic dose of a composition according to the invention.

The compositions according to the invention are useful for treating the seeds of cereals (wheat, rye, triticale and barley in particular), of potato, of cotton, of pea, of rape, of corn or of flax, or the seeds of woodland trees (in particular resiniferous trees) or genetically modified seeds of these plants.

It will be noted in this respect that, in the jargon of the person skilled in the art, the expression "seed treatment" in fact refers to treatment of the grains. The application techniques are well known to those skilled in the art and they may be used without a drawback in the context of the present invention. Mention may be made, for example, of film-cladding or coating. Among the plant multiplication products concerned, mention may be made in particular of seeds or grains, and tubers.

As has been indicated above, the methods for coating the plant multiplication products, in particular the seeds, are well known in the art and in particular involve film-cladding or coating techniques.

The products and compositions according to the invention may also be applied as a foliar application to the plant crops, i.e. to the leaves, the flowers, the fruit and/or the trunks of the plants concerned.

Among the plants targeted by the method according to the invention, mention may be made of rice, corn, cotton, cereals, for instance wheat, barley, triticale, fruit trees, in particular apple trees, pear trees, peach trees, vines, banana trees, orange trees, lemon trees, etc., oil-yielding crops, for example rape and sunflower, market-garden crops and leguminous crops, tomatoes, lettuce, protein-yielding crops, peas, solanacea plants, for example potato, beetroot and flax, and woodland trees, as well as genetically modified homologues of these crops.

Among the plants targeted by the method according to the invention, mention may be made of:
  wheat, as regards controlling the following seed diseases: fusaria (*Microdochium nivale* and *Fusarium roseum*), stinking smut (*Tilletia caries, Tilletia controversa* or *Tilletia indica*), septoria disease (*Septoria nodorum*) and loose smut;
  wheat, as regards controlling the following diseases of the aerial parts of the plant: cereal eyespot (*Tapesia yallundae, Tapesia acuiformis*), take-all (*Gaeumannomyces graminis*), foot blight (*F. culmorum, F. graminearum*), black speck (*Rhizoctonia cerealis*), powdery mildew (*Erysiphe graminis* form a specie *tritici*), rusts (*Puccinia striiformis* and *Puccinia recondita*) and septoria diseases (*Septoria tritici* and *Septoria nodorum*);
  wheat and barley, as regards controlling bacterial and viral diseases, for example barley yellow mosaic;
  barley, as regards controlling the following seed diseases: net blotch (*Pyrenophora graminea, Pyrenophora teres* and *Cochliobolus sativus*), loose smut (*Ustilago nuda*) and fusaria (*Microdochium nivale* and *Fusarium roseum*);
  barley, as regards controlling the following diseases of the aerial parts of the plant: cereal eyespot (*Tapesia yallundae*), net blotch (*Pyrenophora teres* and *Cochliobolus sativus*), powdery mildew (*Erysiphe graminis* form a specie *hordei*), dwarf leaf rust (*Puccinia hordei*) and leaf blotch (*Rhynchosporium secalis*);
  potato, as regards controlling tuber diseases (in particular *Helminthosporium solani, Phoma tuberosa, Rhizoctonia solani, Fusarium solani*), mildew (*Phytopthora infestans*) and certain viruses (virus Y);
  potato, as regards controlling the following foliage diseases: early blight (*Alternaria solani*), mildew (*Phytophthora infestans*);
  cotton, as regards controlling the following diseases of young plants grown from seeds: damping-off and collar rot (*Rhizoctonia solani, Fusarium oxysporum*) and black root rot (*Thielaviopsis basicola*);
  protein-yielding crops, for example peas, as regards controlling the following seed diseases: anthracnose (*Ascochyta pisi, Mycosphaerella pinodes*), fusaria (*Fusarium oxysporum*), grey mould (*Botrytis cinerea*) and mildew (*Peronospora pisi*);
  oil-bearing crops, for example rape, as regards controlling the following seed diseases: *Phoma lingam, Alternaria brassicae* and *Sclerotinia sclerotiorum;*
  corn, as regards controlling seed diseases: (*Rhizopus* sp., *Penicillium* sp., *Trichoderma* sp., *Aspergillus* sp., and *Gibberella fujikuroi*);
  flax, as regards controlling the seed disease: *Alternaria linicola;*
  forest trees, as regards controlling damping-off (*Fusarium oxysporum, Rhizoctonia solani*);
  rice, as regards controlling the following diseases of the aerial parts: blast disease (*Magnaporthe grisea*), bordered sheath spot (*Rhizoctonia solani*);
  leguminous crops, as regards controlling the following diseases of seeds or of young plants grown from seeds: damping-off and collar rot (*Fusarium oxysporum, Fusarium roseum, Rhizoctonia solani, Pythium* sp.);
  leguminous crops, as regards controlling the following diseases of the aerial parts: grey mould (*Botrytis* sp.), powdery mildews (in particular *Erysiphe cichoracearum, Sphaerotheca fuliginea* and *Leveillula taurica*), fusaria (*Fusarium oxysporum, Fusarium roseum*), leaf spot (*Cladosporium* sp.), alternaria leaf spot (*Alternaria* sp.), anthracnose (*Colletotrichum* sp.), septoria leaf spot (*Septoria* sp.), black speck (*Rhizoctonia solani*), mildews (for example *Bremia lactucae, Peronospora* sp., *Pseudoperonospora* sp., *Phytophthora* sp.);
  fruit trees, as regards diseases of the aerial parts: monilia disease (*Monilia fructigenae, M. laxa*), scab (*Venturia inaequalis*), powdery mildew (*Podosphaera leucotricha*);

vine, as regards diseases of the foliage: in particular grey mould (*Botrytis cinerea*), powdery mildew (*Uncinula necator*), black rot (*Guignardia biwelli*) and mildew (*Plasmopara viticola*);

beetroot, as regards the following diseases of the aerial parts: *cercospora* blight (*Cercospora beticola*), powdery mildew (*Erysiphe beticola*), leaf spot (*Ramularia beticola*).

Wheat and rice are the preferred plants for carrying out the method according to the invention, although all the crops, plants, plant multiplication products, flowers, wood and, as a general rule, all the plants which may suffer attack by phytopathogenic fungi, may be advantageously treated according to the method of the invention, by using one or more active materials, fungicidal compositions according to the present invention.

In the case of plant treatments, the dose of composition applied is generally and advantageously between 10 and 800 g/ha, preferably 50 to 300 g/ha of active material for applications in folia treatment. The dose of composition applied is generally and advantageously such that the dose of active material is between 2 and 200 g of active material per 100 kg of seed, preferably between 3 and 150 g per 100 kg in the case of seed treatments. It is clearly understood that the doses indicated above are given as illustrative examples of the invention. A person skilled in the art will know how to tailor the application doses according to the nature of the crop to be treated.

The present invention also relates to a method for curatively or preventively treating, with the aid of one or more compounds according to the invention, or of a composition according to the present invention, against fungal diseases liable to grow on or inside lumber. The term "lumber" means all types of species of wood, and all types of working of this wood intended for construction, for example solid wood, high-density wood, laminated wood, plywood, etc.

Thus, the method for treating lumber according to the invention consists in placing one or more compounds of the present invention, or a composition according to the invention, in contact. This placing in contact may cover the most diverse of forms such as, for example, direct application, spraying, dipping, injection or any other suitable means.

The present invention also relates to the treatment of genetically modified plants with the compounds according to the invention or the agrochemical compositions according to the invention. Genetically modified plants are plants into whose genome a heterologous gene encoding a protein of interest has been stably integrated.

According to the invention, the expression "heterologous gene encoding a protein of interest" essentially means genes which give the transformed plant new agronomic properties, or genes for improving the agronomic quality of the transformed plant.

Among the genes which give the transformed plants new agronomic properties, mention may be made of genes which impart a tolerance to certain herbicides, those which impart a resistance to certain insects, those which impart a tolerance to certain diseases, etc. Such genes are described in particular in patent applications WO 91/02071 and WO 95/06128.

Among the genes which impart a tolerance to certain herbicides, mention may be made of the Bar gene imparting tolerance to bialophos, the gene encoding a suitable EPSPS imparting a resistance to herbicides having EPSPS as target, such as glyphosate and its salts (U.S. Pat. Nos. 4,535,060, 4,769,061, 5,094,945, 4,940,835, 5,188,642, 4,971,908, 5,145,783, 5,310,667, 5,312,910, 5,627,061, 5,633,435 and FR 2 736 926), the gene encoding glyphosate oxidoreductase (U.S. Pat. No. 5,463,175) or a gene encoding an HPPD imparting a tolerance to herbicides having HPPD as target, such as isoxazoles, in particular isoxafutol (FR 95/06800 and FR 95/13570), diketonitriles (EP-A-0 496 630 and EP-A-0 496 631) or triketones, in particular sulcotrioine (EP-A-0 625 505, EP-A-0 625 508 and U.S. Pat. No. 5,506,195). Such genes encoding an HPPD imparting a tolerance to herbicides having HPPD as target are disclosed in patent application WO 96/38567.

In the case of genes encoding EPSPS or HPPD, and more particularly for the above genes, the sequence encoding these enzymes is advantageously preceded by a sequence encoding a transit peptide, in particular for the transit peptide known as optimized transit peptide, disclosed in patent U.S. Pat. No. 5,510,471.

Among the genes imparting novel insect-resistance properties, mention will be made more particularly of the genes encoding the Bt proteins which are widely described in the literature and well known to those skilled in the art. Mention will also be made of the genes encoding proteins extracted from bacteria such as Photorabdus (WO 97/17432 and WO 98/08932).

Among the genes imparting novel disease-resistance properties, mention will be made in particular of the genes encoding chitinases, glucanases and oxalate oxidase, all these proteins and their coding sequences being widely described in the literature, or genes encoding antibacterial and/or antifungal peptides, in particular cysteine-rich peptides containing less than 100 amino acids, such as plant thionines or defensines, and more particularly lytic peptides of all origins comprising one or more disulphide bridges between the cysteines and regions comprising basic amino acids, in particular the following lytic peptides: androctonine (WO 97/30082 and PCT/FR98/01814, filed on 18 Aug. 1998) or drosomicin (PCT/FR98/01462, filed on 8 Jul. 1998). Mention will also be made of the genes encoding fungal elicitor peptides, in particular the elicitins (Kamoun et al., 1993; Panabières et al., 1995).

Among the genes which modify the constitution of modified plants, mention may be made in particular of genes which modify the content and quality of certain essential fatty acids (EP-A-0 666 918) or the content and quality of proteins, in particular in the leaves and/or seeds of the said plants. Mention will be made in particular of the genes encoding proteins that are rich in sulphur-containing amino acids (WO 98/20133; WO 97/41239; WO 95/31554; WO 94/20828 and WO 92/14822).

The present invention relates more particularly to the treatment of genetically modified plants comprising a heterologous gene which gives the plant disease-resistance properties. The heterologous gene preferentially gives the genetically modified plant a spectrum of activity that is complementary to the spectrum of activity of the compounds according to the invention. According to the invention, the expression "complementary spectrum" means a spectrum of activity for the heterologous gene which is different from the spectrum of activity of the compounds according to the invention, or a spectrum of activity relating to identical infectious agents but allowing an identical or improved control for lower application doses of compounds according to the invention.

Lastly, the invention relates to the use of the compounds according to the invention that are useful in human and animal therapy for the treatment of fungal diseases such as, for example, mycoses, dermatoses, trichophyton diseases and candidiases or diseases caused by *Aspergillus spp.*, for example *Aspergillus fumigatus*.

The following Examples illustrate in a non-limiting manner several examples of fungicidal compounds according to the invention. In the Examples which follow, "MP" signifies "melting point" and is expressed in ° Celsius (° C.).

EXAMPLE a)

Preparation of 2-Cyano-3-Methoxy-4-Nitropyridine

A mixture of 12.5 g (12.5 moles) of the N-oxide of 3-methoxy-4-nitropyridine, 7.72 mL (1.1 eq.) of methyl sulphate and 70 mL of 1,2-dichloroethane is heated at 70° C. for 2.5 hours. It is allowed to cool and 70 mL of water are added. It is cooled in a salt and ice bath and, in portions, 7.55 g (2.1 moles) of sodium cyanide are added, controlling the temperature so as not to exceed 10° C. After 4 hours stirring, the reaction mixture is extracted with ethyl ether, the organic phase is washed with water, concentrated and the residue chromatographed (ethyl acetate/dichloromethane). There is obtained 7.06 g of a yellow oil (yield 53%).

EXAMPLE b)

Preparation of 4-Bromo-2-Cyano-3-Methoxypyridine

A mixture of 6 g (0.0335 moles) of 2-cyano-3-methoxy-4-nitropyridine obtained in Example a), 12.37 g (0.100 moles) of acetyl bromide and 36 mL of 1,2-dimethoxyethane is heated at 85° C. for 1.5 hours. It is allowed to cool and the reaction mixture is poured onto 100 g of crushed ice. 30 mL of 1,2-dichloroethane are added and gently neutralised to pH=8 with a 28% aqueous solution of ammonia. After extraction with 1,2-dichloroethane, washing with water, drying and concentration the residue is chromatographed (ethyl acetate/heptane, 3:7) to obtain 5.32 g (75% yield) of a white solid (MP=116° C.).

In a similar manner, replacing the acetyl bromide by acetyl chloride, there is obtained 4-chloro-2-cyano-3-methoxpyridine (83% yield) in the form of a white solid (MP=91° C.).

EXAMPLE c)

Preparation of 4-Azido-2-Cyano-3-Methoxypyridine

To 1 g (0.0155 moles) of sodium azide in 25 mL of dimethylformamide at 0° C., there is added gently 3 g (0.0141 moles) of 4-bromo-2-cyano-3-methoxypyridine from Example b), dissolved in 40 mL of dimethylformamide.

The mixture is stirred for 6 hours at ambient temperature. The reaction mixture is diluted in 200 mL of iced water and extracted with dichloromethane. The organic phase is washed twice with water, dried, concentrated and the residue chromatographed (ethyl acetate/heptane, 3:7). There is obtained 0.87 g (35% yield) of a white solid (MP=102° C.).

EXAMPLE d)

Preparation of 4-Chloro-3-Hydroxypicolinic Acid

A mixture of 2 g (0.012 moles) of 4-chloro-2-cyano-3-methoxypyridine obtained in Example b), and 7 mL of 37% hydrochloric acid is heated at 100° C. for 12 hours. After cooling the solid formed is filtered, washed once with water and 3 times with acetone and dried under vacuum for 8 hours. There is obtained 1.78 g (86% yield) of a yellow solid (MP=228° C.)

In the same manner, the following hydroxy acids are obtained:

| Y | Hydracid | Yield, MP (° C.) |
|---|---|---|
| 4-bromo-3-hydroxy-picolinic acid | HBr | Yellow solid, 82%, 230° C. |
| 4-azido-3-hydroxy-picolinic acid | HCl | Violet solid, 63% |
| 3,4-dihydroxypicolinic acid | HBr | White solid, 74%, 264° C. |

EXAMPLE e)

Preparation of 2-Cyano-3,4-Dimethoxypyridine 3 g (0.017 moles) of 2-cyano-3-methoxy-4-nitropyridine obtained in Example a) and a sodium methoxide solution prepared from 0.77 g (0.033 moles) of sodium and 65 mL of methanol are stirred at ambient temperature for 4 hours. There is added 100 mL of water, the methanol is eliminated and the aqueous phase is extracted with dichloromethane. The organic phase is washed with water, dried, concentrated and the residue chromatographed (ethyl acetate/heptane, 1:1) to obtain 1.96 g (72% yield) of a white solid (MP=133° C.).

EXAMPLE f)

Preparation of 2-Cyano-3-Hydroxy-4-Thiomethoxypyridine 2 g of 4-bromo-2-cyano-3-methoxypyridine obtained in Example b) and 2.16 g of sodium thiomethoxide in 40 mL of anhydrous dimethylformamide are heated at 85° C. for 5 hours. After cooling and the addition of 20 mL of water, the reaction mixture is concentrated to dryness. The residue is extracted three times with hot methanol. The cooled methanolic phase is filtered and concentrated. There is obtained 1.51 g (97% yield) of a brown syrup used crude.

EXAMPLE g)

Preparation of 3-Hydroxy-4-Thiomethoxypicolinic Acid 2.5 g (0.015 moles) of 2-cyano-3-hydroxy-4-thiomethoxypyridine from Example f), 8.5 g of potassium hydroxide and 25 mL of water are heated at reflux for 2.5 hours. After allowing to cool and in an ice bath the mixture is gently neutralised with 1N hydrochloric acid to pH=2-3. The solid formed is filtered. The solid is washed once with water and three times with acetone; it is dried under vacuum for 8 hours. There is obtained 1.81 g (68% yield) of a white solid (MP=247° C.).

EXAMPLE h)

Preparation of 3,4-Dimethoxypicolinic acid 1 g of 3,4-dimethoxy-2-cyanopyridine obtained in Example e) and 3.5 g of potassium hydroxide in 15 mL of water are heated to 85° C. for half an hour. It is allowed to cool and in an ice bath hydrochloric acid is added gently to pH=2-3. After concentration to dryness, the residue is extracted three times with hot methanol, allowed to cool, filtered and concentrated. There is obtained a solid used crude.

EXAMPLE i)

Preparation of the N-xide of 3-Hydroxypicolinic acid

To a mixture of 20 ml acetic acid and 20 ml Of hydrogen peroxide solution, are added 2 g of 3-hydroxypicolinic acid; the whole is heated at 80° C. for 5 hours. After elimination of the solvents under vacuum, the solid obtained is washed with hot alcohol to obtain 2.02 g of compound in the form of a white solid (MP=182° C.).

PREPARATION EXAMPLE

3-Hydroxy-4-Methoxy-N-Para-Phenoxyphenylpicolinamide 0.046 g of para-phenoxyaniline, 0.04 g of 3-hydroxy-4-methoxypicolinic acid (obtained in a manner similar to that described in Example g)), 0.034 g of 1-hydroxybenzotriazole and 0.060 g of 1-(3-dimethylaminopropyl)-3-ethylcarbodiimide hydrochloride are heated in 2 mL of pyridine between 75 and 85° C. for 1 to 2 hours. After cooling, the residue is taken up in a mixture of dichloromethane and 2 mL of 1N hydrochloric acid. After extraction with dichloromethane, concentration and chromatography on silica there is obtained 0.057 g of the title compound, a yellow solid (MP=186° C.).

EXAMPLE 1

Compound No. 76

4-Amino-3-Hydroxy-N-Para-Phenoxyphenylpicolinamide

To 0.14 g of 4-azido-3-hydroxy-N-para-phenoxyphenylpicolinamide (obtained from the compound of the Preparation Example according to the methods described in Examples a) to g)) dissolved in a mixture of ethanol/ethyl acetate, 1:2, there is added a spatula tip of 10% palladium on carbon. Hydrogenation is carried out at 20 bars pressure and ambient temperature for 4-5 hours. After filtration, concentration and chromatography of the residue in ethyl acetate, there is obtained 0.099 g of a white solid (MP : 197° C.).

EXAMPLE 2

Compound No. 111

4-Formamido-3-Hydroxy-N-Para-Phenoxyphenylpicolinamide

There is heated at reflux 61.2 mg of acetic anhydride and 27.6 mg of formic acid for 4 hours and 46 mg of 4-amino-3-hydroxy-N-para-phenoxyphenylpicolin-amide of Example 1 is added, dissolved in 5 mL of tetrahydrofuran. After 8 hours at reflux, the reaction mixture is concentrated and purified by chromatography to give 39 mg of a yellow solid MP 208° C.

EXAMPLE 3

Compound No. 108

4-Amino-3-Hydroxy-N-Para-[4-(Trifluoromethyl)Phenoxy]-Henylpicolinamide

Stage 1:

4-azido-3-iodo-N-para-[4-(trifluoromethyl)phenoxy]phenylpicolinamide

A mixture of 25.9 g (0.05 mol) of 4-chloro-3-iodo-N-para-[4-(trifluoromethyl)phenoxy]-phenylpicolinamide (prepared from picolinic acid according to the method described in Heterocycles, 47, (1998), 811) and 6.5 g (0.1 mol) of sodium azide dissolved in 50 mL of dimethyl sulphoxide is heated to 70° C. for 8 hours. After cooling, the mixture is poured into 1 liter of water. The precipitate obtained is filtered and washed with ether. There is obtained 22.5 g (85% yield) of a brown solid. Rf (heptane/ethyl acetate 50/50): 0.45.

Stage 2:

4-amino-3-hydroxy-N-para-[4-(trifluoromethyl)-phenoxy]phenylpicolinamide

A mixture of 21.0 g (0.04 mol) of 4-azido-3-iodo-N-para-[4-(trifluoromethyl)phenoxy]-phenylpicolinamide and of 21.0 g (0.08 mol) of triphenylphosphine in 80 mL of tetrahydrofuran, is stirred at ambient temperature for 15 hours. The mixture is hydrolysed for 1 hour with 100 mL of a solution of 1N hydrogen chloride. The mixture is then poured into 200 mL of water and neutralised by the addition of 100 mL of 1N sodium hydroxide. After extraction with ethyl acetate, drying and concentration, the residue is chromatographed on silica gel (ethyl acetate/heptane 1:1) to obtain 13.4 g (55% yield) of a yellow solid. Rf (heptane/ethyl acetate 50/50):0.29.

Stage 3:

4-amino-3-hydroxy-N-para-[4-(trifluoromethyl)phenoxy]phenylpicolinamide

A mixture of 9.15 g (0.018 mol) of 4-amino-3-iodo-N-para-[4-(trifluoromethyl)phenoxy]phenylpicolinamide dissolved in 82 ml of a 50% aqueous solution of potassium hydroxide and 20 mL of dimethyl sulphoxide is heated for 8 hours at 90° C. The medium is poured onto 100 mL of water and extracted with ether. The organic phase is dried and separated. After recrystallisation in methanol, there is obtained 6.15 g (85% yield) of a white solid (MP=202° C.).

The compounds described in the following Tables 1 and 2 are prepared in a similar manner:

TABLE 1

[Structure: pyridine with Y at 4-position, G-Z at 3-position, C(=O)-Q2 at 2-position]

| N° | Q2 | G—Z | Y | MP |
|---|---|---|---|---|
| 1 | 4-phenoxyphenyl-NH- | HO- (with CH3, CH3) | Br (with CH3, CH3) | 140 |
| 2 | 4-(4-methylphenoxy)phenyl-NH- | -OH (with CH3, CH3) | Br (with CH3, CH3) | 168 |
| 3 | 4-(4-chlorophenoxy)phenyl-NH- | -OH (with CH3, CH3) | Br (with CH3, CH3) | 155 |
| 4 | 4-(4-trifluoromethylphenoxy)phenyl-NH- | -OH (with CH3, CH3) | Br (with CH3, CH3) | 145 |
| 5 | 4-(3-trifluoromethylphenoxy)phenyl-NH- | -OH (with CH3, CH3) | Br (with CH3, CH3) | 118 |
| 6 | 4-(2,6-di-sec-butylphenoxy)phenyl-NH- | -OH (with CH3, CH3) | Br (with CH3, CH3) | 86 |

TABLE 1-continued
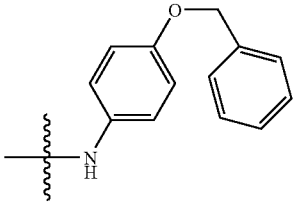
| N° | Q2 | G—Z | Y | MP |
|---|---|---|---|---|
| 7 | 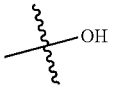 |  —OH | 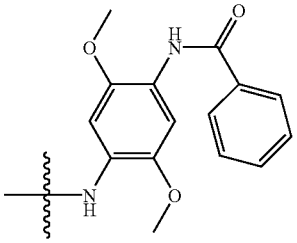 Br | 165 |
| 8 | 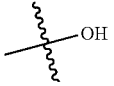 |  —OH | 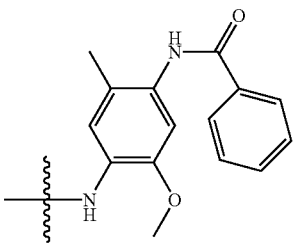 Br | 250 |
| 9 | 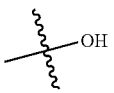 |  —OH | 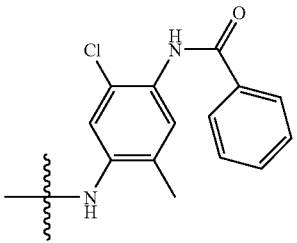 Br | 255 |
| 10 | 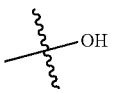 |  —OH | 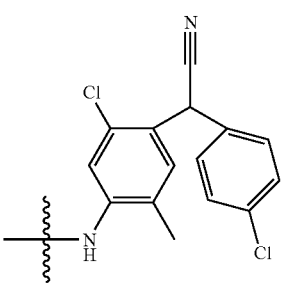 Br | 235 |
| 11 | 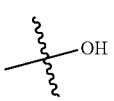 |  —OH | Br | 162 |

TABLE 1-continued
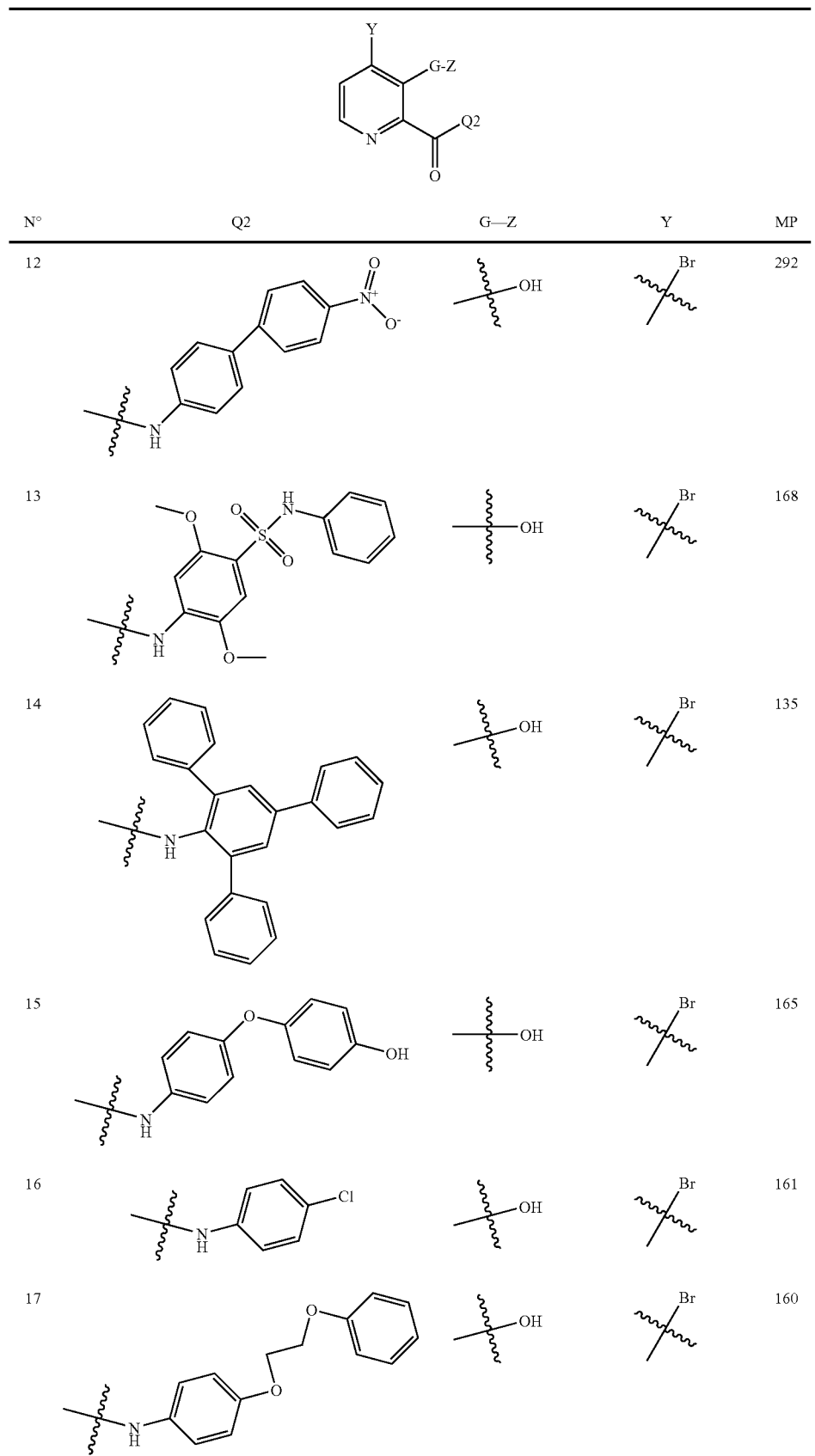
| N° | Q2 | G—Z | Y | MP |
|---|---|---|---|---|
| 12 | 4'-nitro-biphenyl-4-yl-NH- | —OH | Br | 292 |
| 13 | 2,5-dimethoxy-4-(phenylsulfamoyl)phenyl-NH- | —OH | Br | 168 |
| 14 | 2,4,6-triphenylphenyl-NH- | —OH | Br | 135 |
| 15 | 4-(4-hydroxyphenoxy)phenyl-NH- | —OH | Br | 165 |
| 16 | 4-chlorophenyl-NH- | —OH | Br | 161 |
| 17 | 4-(2-phenoxyethoxy)phenyl-NH- | —OH | Br | 160 |

TABLE 1-continued
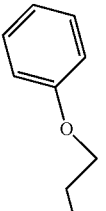
| N° | Q2 | G—Z | Y | MP |
|---|---|---|---|---|
| 18 | 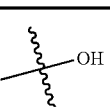 |  | 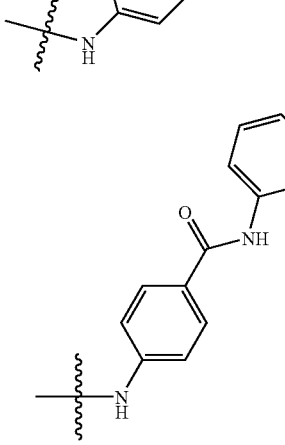 | 122 |
| 19 | 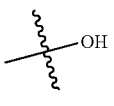 |  | 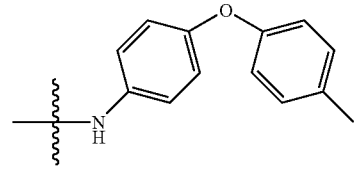 | 256 |
| 20 | 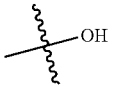 |  | 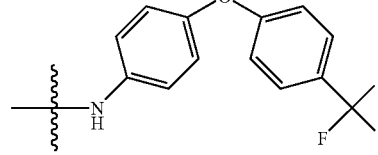 | 198 |
| 21 | 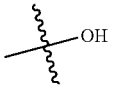 |  | 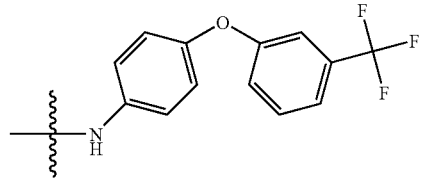 | 162 |
| 22 | 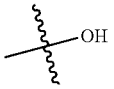 |  | | 139 |

TABLE 1-continued
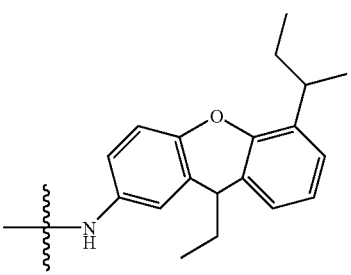
| N° | Q2 | G—Z | Y | MP |
|----|----|----|---|----|
| 23 |  |  —OH | 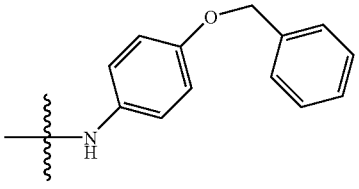 S | 150 |
| 24 |  |  —OH | 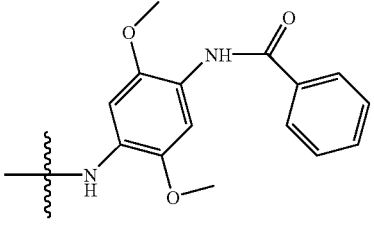 S | 208 |
| 25 |  |  —OH | 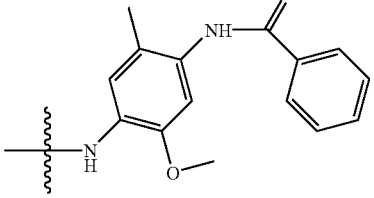 S | 210 |
| 26 |  |  —OH | 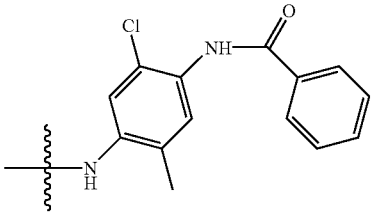 S | 242 |
| 27 |  |  —OH | S | 243 |

TABLE 1-continued
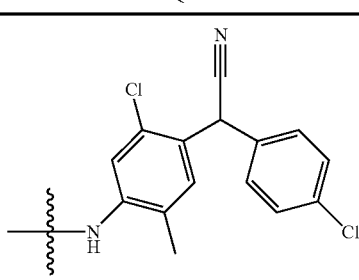
| N° | Q2 | G—Z | Y | MP |
|---|---|---|---|---|
| 28 |  |  —OH | 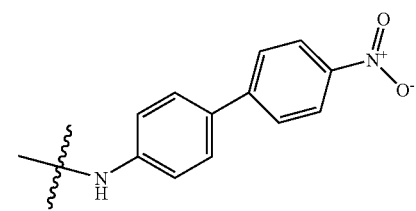 | 212 |
| 29 |  |  —OH | 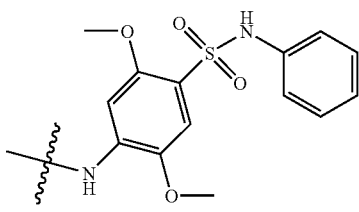 | |
| 30 |  |  —OH | 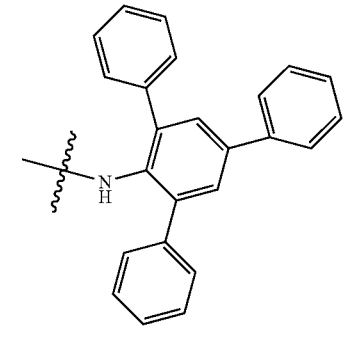 | 185 |
| 31 |  |  —OH | 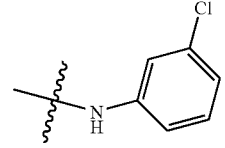 | 118 |
| 32 |  |  —OH | 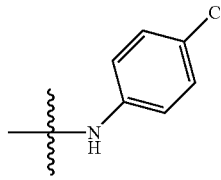 | 172 |
| 33 |  |  —OH | | 214 |

TABLE 1-continued
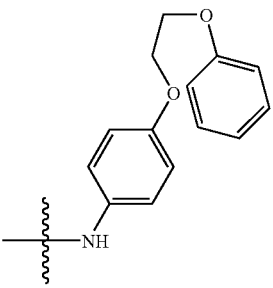
| N° | Q2 | G—Z | Y | MP |
|---|---|---|---|---|
| 34 | 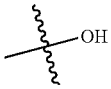 |  —OH | 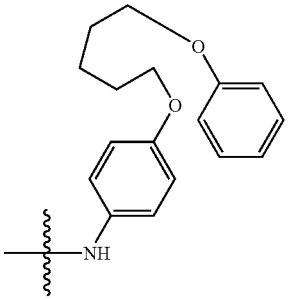 | 172 |
| 35 | 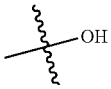 |  —OH | 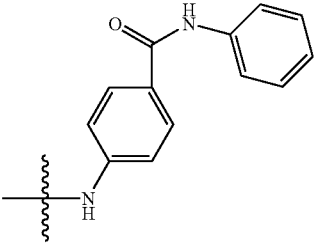 | 122 |
| 36 | 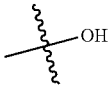 |  —OH | 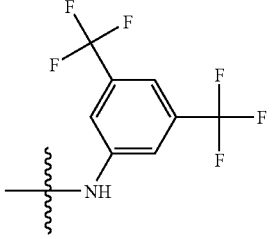 | 248 |
| 37 | 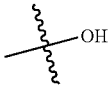 |  —OH | | 168 |

TABLE 1-continued
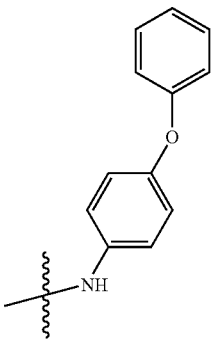
| N° | Q2 | G—Z | Y | MP |
|---|---|---|---|---|
| 38 | 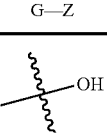 |  | 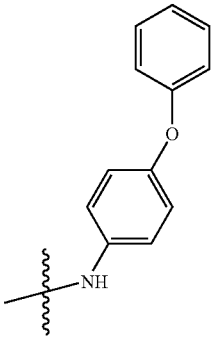 | 186 |
| 39 | 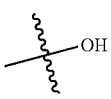 |  | 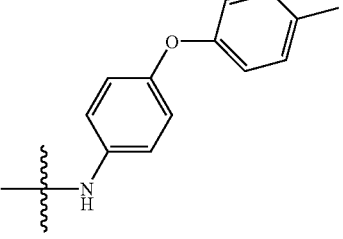 | 120 |
| 40 | 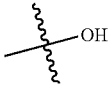 |  | 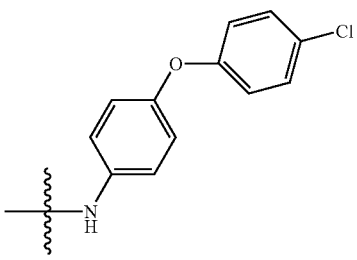 | 146 |
| 41 | 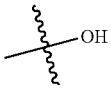 |  | | 148 |

TABLE 1-continued

| N° | Q2 | G—Z | Y | MP |
|---|---|---|---|---|
| 42 | 4-(4-(trifluoromethyl)phenoxy)phenyl-NH- | —OH | Cl | 147 |
| 43 | 4-(3-(trifluoromethyl)phenoxy)phenyl-NH- | —OH | Cl | 110 |
| 44 | 4-(2,6-di-sec-butylphenoxy)phenyl-NH- | —OH | Cl | 66 |
| 45 | 4-(benzyloxy)phenyl-NH- | —OH | Cl | 150 |

TABLE 1-continued
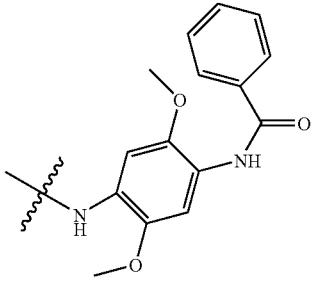
| N° | Q2 | G—Z | Y | MP |
|---|---|---|---|---|
| 46 |  |  OH | 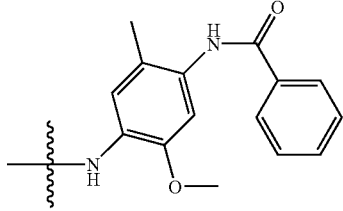 Cl | 246 |
| 47 |  |  OH | 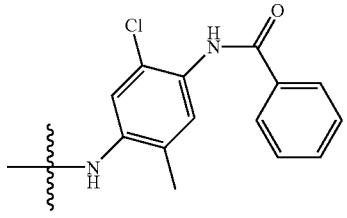 Cl | 260 |
| 48 |  |  OH | 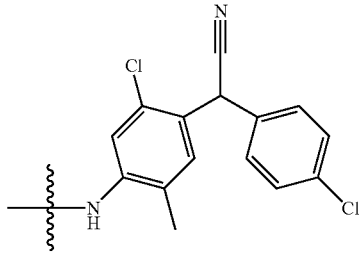 Cl | 226 |
| 49 |  |  OH | 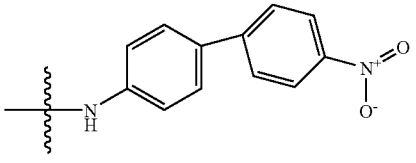 Cl | 140 |
| 50 |  |  OH | Cl | |

TABLE 1-continued
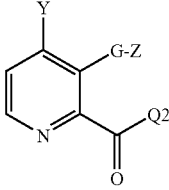
| N° | Q2 | G—Z | Y | MP |
|---|---|---|---|---|
| 51 |  | —OH | Cl | 166 |
| 52 |  | —OH | Cl | 124 |
| 53 |  | —OH | Cl | 174 |
| 54 |  | —OH | Cl | 166 |
| 55 |  | —OH | Cl | 164 |

TABLE 1-continued

| N° | Q2 | G—Z | Y | MP |
|---|---|---|---|---|
| 56 | (4-(5-phenoxypentyloxy)phenyl)amino | OH | Cl | 120 |
| 57 | (4-(phenylcarbamoyl)phenyl)amino | OH | Cl | 279 |
| 58 | (3,5-bis(trifluoromethyl)phenyl)amino | OH | Cl | 76 |
| 59 | (4-(2-phenoxyethoxy)phenyl)amino | OH | Cl | 156 |
| 60 | (4-phenoxyphenyl)amino | OH | OH | 284 |

TABLE 1-continued

| N° | Q2 | G—Z | Y | MP |
|---|---|---|---|---|
| 61 | 4-(4-methylphenoxy)phenyl-NH- | -C(CH3)2-OH | OH | 265 |
| 62 | 4-phenoxyphenyl-NH- | HO-C(CH3)2- | N3 | 138 |
| 63 | 4-(3-trifluoromethylphenoxy)phenyl-NH- | HO-C(CH3)2- | N3 | — |
| 64 | 4-(4-chlorophenoxy)phenyl-NH- | -C(CH3)2-OH | OH | 271 |
| 65 | 4-(4-trifluoromethylphenoxy)phenyl-NH- | -C(CH3)2-OH | OH | 274 |
| 66 | 4-(3-trifluoromethylphenoxy)phenyl-NH- | -C(CH3)2-OH | OH | 252 |
| 67 | bis(sec-butyl)diphenyl ether-NH- | -C(CH3)2-OH | OH | 272 |

TABLE 1-continued
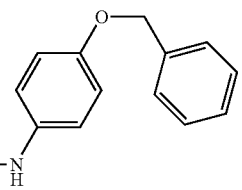
| N° | Q2 | G—Z | Y | MP |
|---|---|---|---|---|
| 68 |  |  —OH | 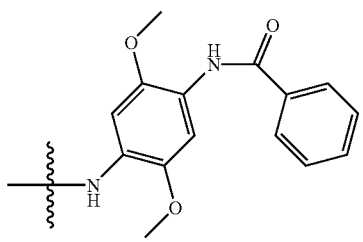 OH | 294 |
| 69 |  |  —OH | 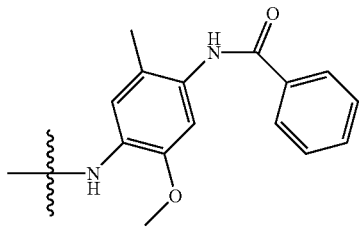 OH | 296 |
| 70 |  |  —OH | 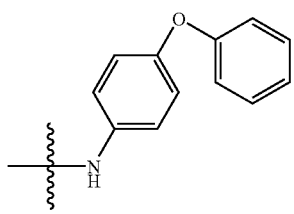 OH | |
| 71 |  |  O— | 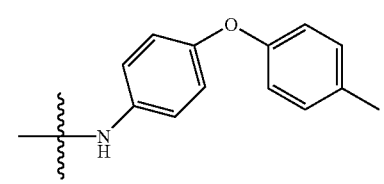 S— | |
| 72 |  |  O— | 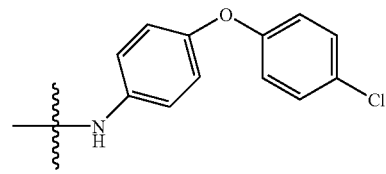 S— | 102 |
| 73 |  |  O— | | 114 |

TABLE 1-continued

| N° | Q2 | G—Z | Y | MP |
|---|---|---|---|---|
| 74 | 2,6-diisopropylphenoxy-phenyl-NH- | —O— | —S— | |
| 75 | 4-(3-trifluoromethylphenoxy)phenyl-NH- | —O— | —S— | 136 |
| 76 | 4-phenoxyphenyl-NH- | —OH | —NH₂ | 197 |
| 77 | 4-(3-trifluoromethylphenoxy)phenyl-NH- | —OH | —NH₂ | 199 |
| 78 | 2-chloro-5-methyl-4-(benzamido)phenyl-NH- | —OH | —OH | |

TABLE 1-continued

| N° | Q2 | G—Z | Y | MP |
|---|---|---|---|---|
| 79 | 2-chloro-5-methyl-4-(NH-)phenyl-α-(4-chlorophenyl)-α-cyano | —C(CH₃)₂—OH | OH | 148 |
| 80 | 4'-nitro-biphenyl-4-yl-NH— | —C(CH₃)₂—OH | OH | |
| 81 | 3-chlorophenyl-NH— | —C(CH₃)₂—OH | OH | 277 |
| 82 | 4-chlorophenyl-NH— | —C(CH₃)₂—OH | OH | 288 |
| 83 | 3,5-bis(trifluoromethyl)phenyl-NH— | —C(CH₃)₂—OH | OH | 278 |
| 84 | 4-(phenylcarbamoyl)phenyl-NH— | —C(CH₃)₂—OH | OH | |

TABLE 1-continued
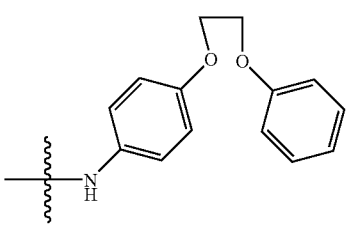
| N° | Q2 | G—Z | Y | MP |
|---|---|---|---|---|
| 85 | 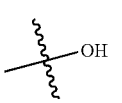 |  OH | 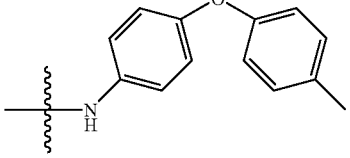 OH | 276 |
| 86 | 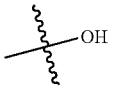 | 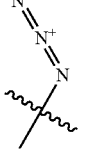 OH | 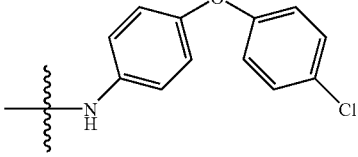 N₃ | 121 |
| 87 | 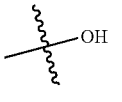 | 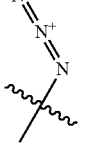 OH | 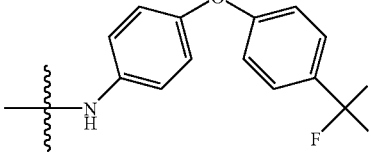 N₃ | 113 |
| 88 | 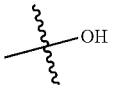 |  OH | 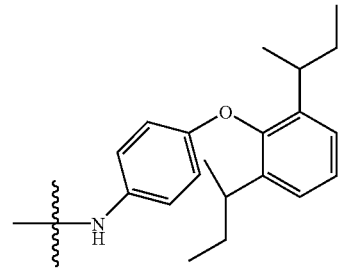 N₃ | 105 |
| 89 | 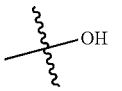 | 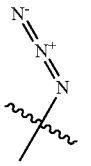 OH | N₃ | 106 |
| 90 | 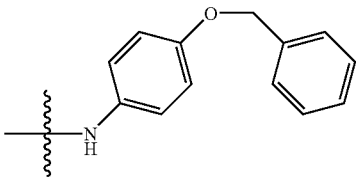 | 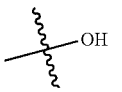 OH | 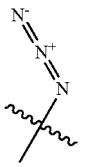 N₃ | 135 |

TABLE 1-continued
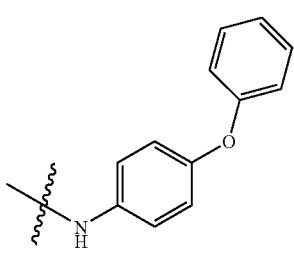
| N° | Q2 | G—Z | Y | MP |
|---|---|---|---|---|
| 91 | 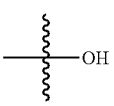 | 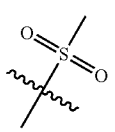 —OH | 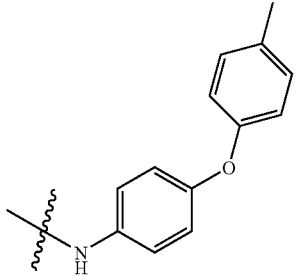 | |
| 92 | 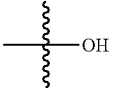 | 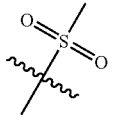 —OH | 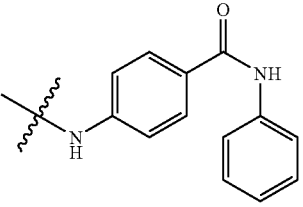 | |
| 93 | 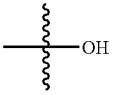 | 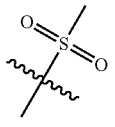 —OH | 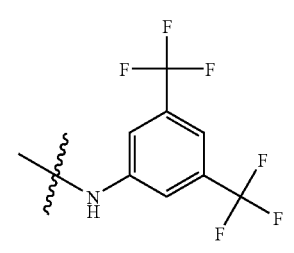 | |
| 94 | 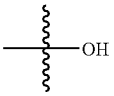 | 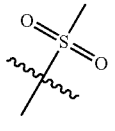 —OH | 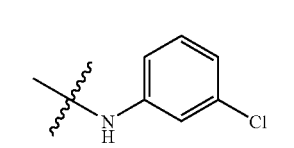 | 170 |
| 95 | 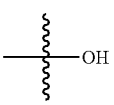 | 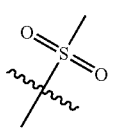 —OH | 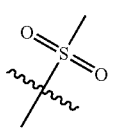 | 142 |

TABLE 1-continued
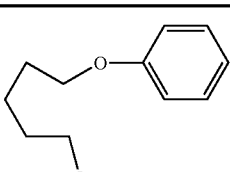
| N° | Q2 | G—Z | Y | MP |
|----|----|----|----|----|
| 96 | 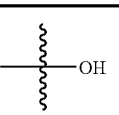 | 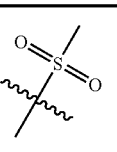 —OH | 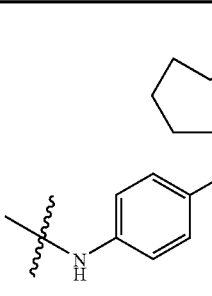 | |
| 97 | 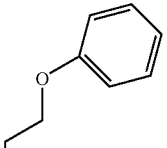 | 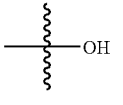 —OH | 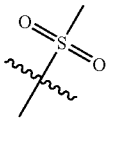 | |
| 98 | 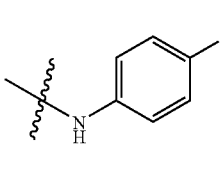 | 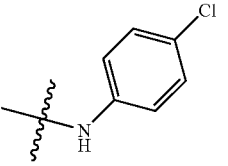 —OH | 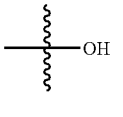 | |
| 99 | 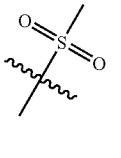 |  —OH | 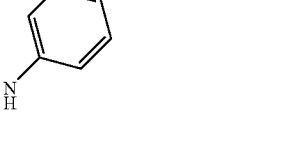 | |
| 100 |  |  —OH | 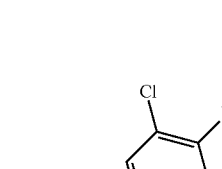 | |

TABLE 1-continued

| N° | Q2 | G—Z | Y | MP |
|---|---|---|---|---|
| 101 | 2-methyl-5-benzamido-4-methoxy-anilino | —OH | methylsulfonyl | |
| 102 | 2,5-dimethoxy-4-benzamido-anilino | —OH | methylsulfonyl | |
| 103 | 4-benzyloxy-anilino | —OH | methylsulfonyl | |
| 104 | 4-(2,6-di-sec-butyl-phenoxy)-anilino | —OH | methylsulfonyl | 117 |

TABLE 1-continued

| N° | Q2 | G—Z | Y | MP |
|---|---|---|---|---|
| 105 | 3-(trifluoromethyl)phenoxy-phenyl-NH— | —OH | —S(O)₂CH₃ | |
| 106 | 4-benzyloxy-phenyl-NH— | —OH | —NH₂ | 214 |
| 107 | 4-(4-chlorophenoxy)-phenyl-NH— | —OH | —NH₂ | 252 |
| 108 | 4-(4-trifluoromethylphenoxy)-phenyl-NH— | —OH | —NH₂ | 232 |
| 109 | (sec-butyl-ethyl-dibenzofuran)-NH— | —OH | —NH₂ | 246 |
| 110 | 4-(4-methylphenoxy)-phenyl-NH— | —OH | —NH₂ | 227 |

TABLE 1-continued
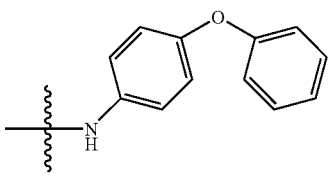
| N° | Q2 | G—Z | Y | MP |
|---|---|---|---|---|
| 111 | 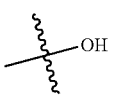 | 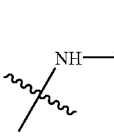 OH | 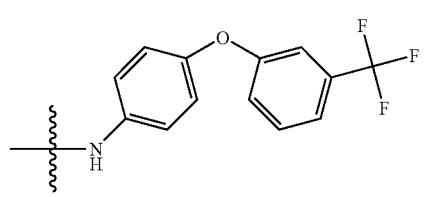 | 208 |
| 112 | 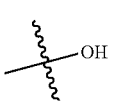 | 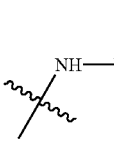 OH | 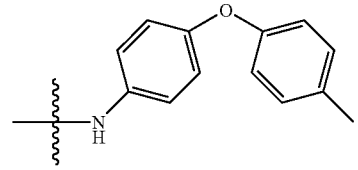 | 208 |
| 113 | 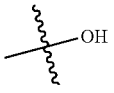 | 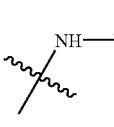 OH | 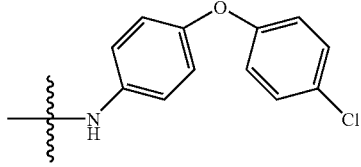 | 185 |
| 114 | 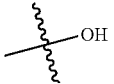 | 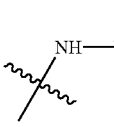 OH | 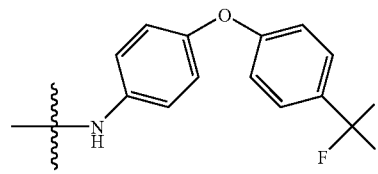 | 198 |
| 115 | 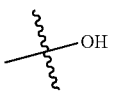 | 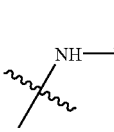 OH | 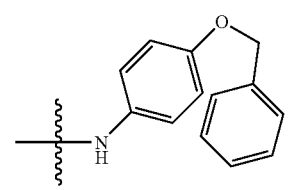 | 173 |
| 116 | 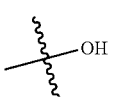 | 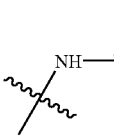 OH | 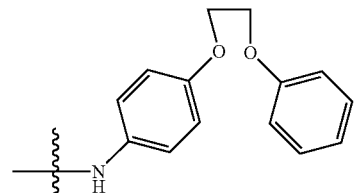 | 170 |
| 117 | 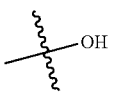 | 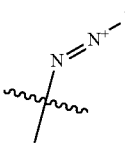 OH | $N=N^+=N^-$ | 143 |

TABLE 1-continued

| N° | Q2 | G—Z | Y | MP |
|---|---|---|---|---|
| 118 | 4-(2-phenyl-1,3-dioxolan-2-yl)phenyl-NH- | -C(CH₃)₂-OH | -NH₂ | 230 |
| 119 | 4-chlorophenyl-NH- | -C(CH₃)₂-OH | -N₃ | 128 |
| 120 | 4-(2-phenyl-1,3-dioxolan-2-yl)phenyl-NH- | -C(CH₃)₂-OH | -NHCHO | 232 |
| 121 | 4-chlorophenyl-NH- | -C(CH₃)₂-OH | -NH₂ | |
| 122 | 4-phenoxyphenyl-NH- | -C(CH₃)₂-OH | -NHC(O)CH₃ | |
| 123 | 4-(4-methylphenoxy)phenyl-NH- | -C(CH₃)₂-OH | -NHC(O)CH₃ | |
| 124 | 4-(4-trifluoromethylphenoxy)phenyl-NH- | -C(CH₃)₂-OH | -NHC(O)CH₃ | |

TABLE 1-continued

| N° | Q2 | G—Z | Y | MP |
|---|---|---|---|---|
| 125 | -NH-C6H4-O-C6H4-CF3 | -OH | -NH-C(O)-CH3 | |
| 126 | -NH-C6H4-O-C6H4- | -O-Et | -NH-CH2-C6H5 | |
| 127 | -NH-C6H4-O-C6H4- | -O-Me | piperidinyl | |
| 128 | -NH-C6H4-O-C6H4- | -OH | piperidinyl | |
| 129 | -NH-C6H4-O-C6H4- | -O-Et | piperidinyl | |
| 130 | -NH-C6H4-O-C6H4- | -OH | -N(CH3)- | |
| 131 | -NH-C6H4-O-C6H4- | -O-Me | -N(CH2-C6H5)- | |
| 132 | -NH-C6H4-O-C6H4- | -OH | -NH-CH2-C6H5 | |

TABLE 1-continued

| N° | Q2 | G—Z | Y | MP |
|---|---|---|---|---|
| 133 | —NH—C₆H₄—O—C₆H₄—CH₃ | —O—CH₃ | NH₂ | |

TABLE 2

| N° | Q2 | G—Z | Y | X2 | MP |
|---|---|---|---|---|---|
| 134 | —NH—C₆H₄—O—C₆H₄—Cl | —OH | —H | —H | 156 |
| 135 | —NH—C₆H₄—O—C₆H₄—CH₃ | —OH | —H | —H | 158 |
| 136 | —NH-(2-methyl-4-methoxy-5-benzamido)phenyl | —OH | —H | —H | 258 |
| 137 | benzamido-2,5-dimethoxy-phenyl-NH— | HO— | —H | —H | 244 |

TABLE 2-continued
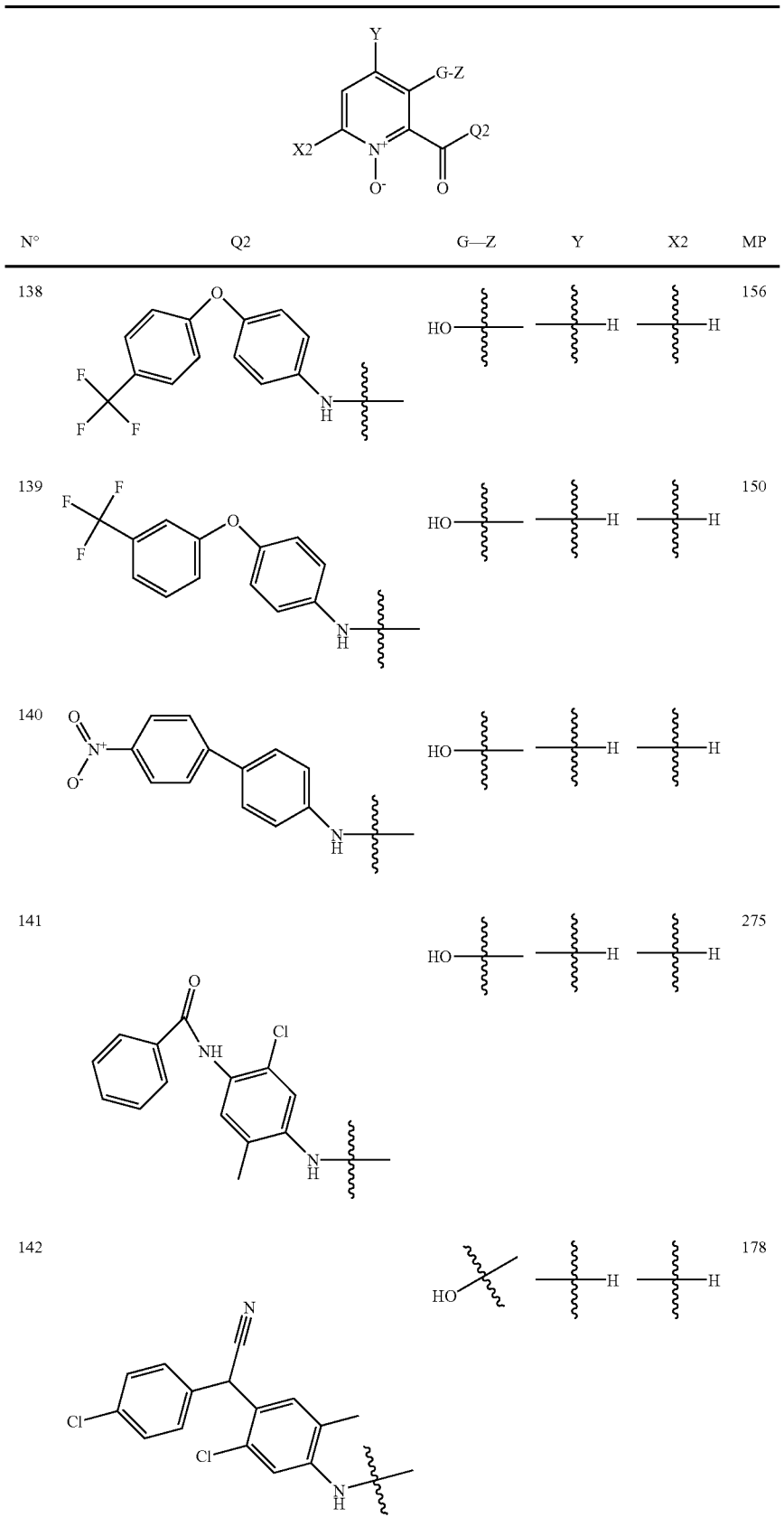

TABLE 2-continued

| N° | Q2 | G—Z | Y | X2 | MP |
|---|---|---|---|---|---|
| 143 | -NH-C6H4-O-CH2-C6H5 | -C(OH)< | H | H | 114 |
| 144 | -NH-C6H4-O-C6H5 | -C(OH)< | H | H | 128 |
| 145 | -NH-C6H4-O-C6H5 | H | H | Br | 120 |
| 146 | -NH-C6H4-O-CH2-C6H5 | H | H | Br | 146 |
| 147 | -NH-C6H4-O-(2,6-di-sec-butyl-C6H3) | -C(OH)< | H | H | — |

TABLE 2-continued
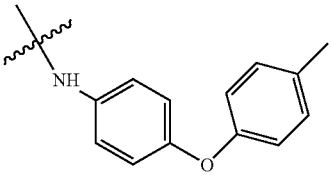
| N° | Q2 | G—Z | Y | X2 | MP |
|---|---|---|---|---|---|
| 148 | 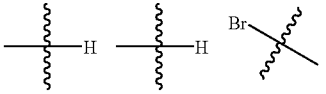 | —H | —H | Br | 151 |
| 149 |  | —H | —H | Br | 142 |
| 150 |  | —H | —H | Br | 155 |
| 151 | 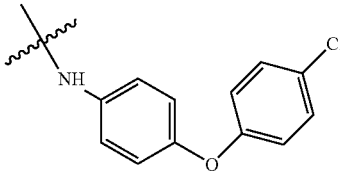 | —H | —H | Br | 126 |
| 152 | 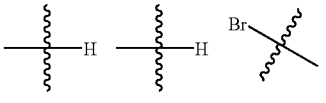 | —H | —H | Br | 140 |
| 153 |  | —H | —H | Br | 262 |

TABLE 2-continued

| N° | Q2 | G—Z | Y | X2 | MP |
|---|---|---|---|---|---|
| 154 | (4-NH-, 2,5-dimethoxy, N-benzoyl aniline) | H | H | Br | 251 |
| 155 | (4-NH-, 5-methoxy, 2-methyl, N-benzoyl aniline) | H | H | Br | 239 |
| 156 | (3,5-bis(trifluoromethyl)anilino) | OH | H | H | 176 |
| 157 | (2-chloroanilino) | OH | H | H | 178 |
| 158 | (3-chloroanilino) | OH | H | H | 172 |
| 159 | (4-chloroanilino) | OH | H | H | 160 |

EXAMPLE 4

Compound No. 171

4-chloro-3-mercapto-N-para-[3-(trifluoromethyl)-phenoxy]phenylpicolinamide

To a solution of 100 mg (0.25 mmol) of 4-chloro-N-para-[3-(trifluoromethyl)phenoxy]phenylpicolinamide (prepared from picolinic acid according to the method described in Heterocycles, 47, (1998), 811) in 2 mL of anhydrous tetrahydrofuran at −78° C., is added 0.32 mL of a commercial 2M solution of lithium diisopropylamide in 15 minutes. After 1 hour of stirring at −78° C., 103 mg (0.40 mmol) of sulphur are added. The mixture is stirred again for 3 hours at −78° C. then treated with an aqueous saturated solution of ammonium chloride. The cold bath is then removed. The two phases are separated and the aqueous phase is extracted with dichloromethane (2×1 mL). The combined organic phases are dried over anhydrous magnesium sulphate and concentrated. The residue is purified by chromatography on silica gel (dichloromethane/methanol, 97:3). There is obtained 61 mg (57% yield) of an orange solid (APCI−, 423, M−1).

EXAMPLE 5

Compound No. 186

4-chloro-3-{[(4-methoxyphenyl)methyl]thio}-N-para-[3-(trifluoromethyl)phenoxy]phenylpicolinamide To a solution of 3.71 9 (8.73 mmol) of 4-chloro-3-mercapto-N-para-[3-(trifluoromethyl)phenoxy]-phenylpicolinamide and of 1.21 mL (1 eq.) of triethylamine in 75 mL of tetrahydrofuran there is added slowly 1.38 mL of 4-methoxybenzyl chloride. After 24 hours stirring at ambient temperature the reaction mixture is washed with water, the organic phase is dried over anhydrous magnesium sulphate and evaporated. The residue is purified by chromatography on silica gel (ethyl acetate/heptane, 50:50). There is obtained 2.94 g (62% yield) of a brown oil (APCI+, 545, M+1).

EXAMPLE 6

Compound No. 199

4-azido-3-{[(4-methoxyphenyl)methyl]thio}-N-para-[3-(trifluormethyl)phenoxy]phenylpicolinamide A mixture of 50 mg (0.092 mmol) of 4-chloro-3-{[(4-methoxyphenyl) methyl]thio}-N-para [3-(trifluoromethyl) phenoxy]phenylpicolinamide, of 30 mg (5 eq.) of sodium azide and of 1 mL of dimethylformamide is heated at 60° C. for 5 days. After cooling, the solvent is evaporated under vacuum and the residue is purified by chromatography on silica gel (ethyl acetate/heptane 50:50). There is obtained 29 mg (57% yield) of a yellow oil (APCI+, 552, M+1).

EXAMPLE 7

Compound No. 207

Preparation of 4-amino-3-mercapto-N-para-[3-(trifluoromethyl)phenoxy]phenylpicolinamide To a solution of 200 mg (0.36 mmol) of 4-azido-3-{[(4-methoxyphenyl) methyl]thio}-N-para-[3-(trifluoromethyl) phenoxy]phenylpicolinamide in 4 mL of tetrahydrofuran, is added 228 mg (2.4 eq.) of triphenylphosphine. The mixture is stirred for 18 hours at ambient temperature, then treated with 1 mL of a 5% aqueous solution of hydrochloric acid. After 10 minutes, the two phases are separated and the organic phase is washed with water, dried over anhydrous magnesium sulphate and concentrated. The residue is purified by chromatography on silica gel (ethyl acetate/heptane, 50:50). There is obtained 99 mg (68% yield) of a white solid (APCI−, 404, M−1).

EXAMPLE 8

Compound No. 190

4-iso-butylamino-3-{[(4-methoxyphenyl)methyl]thio}-N-para-[3-(trifluoromethyl)phenoxy]phenylpicolinamide A solution of 50 mg (0.092 mmol) of 4-chloro-3-{[(4-methoxyphenyl) methyl]thio}-N-para-[3-(trifluoromethyl) phenoxy]phenylpicolinamide in 1 mL of iso-butylamine is heated at 60° C. for 24 hours. After cooling, the excess amine is evaporated and the residue is purified by chromatography on silica gel (ethyl acetate/heptane, 50:50). There is obtained 29 mg (54% yield) of a colourless oil (APCI+, 582, M+1).

EXAMPLE 9

Compound No. 198

4-iso-butyiamino-3-mercapto-N-para-[3-(trifluoromethyl) phenoxy]phenyl picolinamide A solution of 25 mg (0.043 mmol) of 4-iso-butylamino-3-{[(4-methoxyphenyl) methyl]thio}-N-para-[3-(trifluoromethyl) phenoxy] phenylpicolinamide and of 45 mL (10 equivalents) of meta-cresol in 0.6 mL of trifluoroacetic acid is heated to 70° C. for 24 hours. After cooling, the trifluoroacetic acid is evaporated and the residue is gently basified with a saturated aqueous solution of sodium bicarbonate. The mixture is neutralised to pH=7 with a saturated aqueous solution of ammonium chloride and extracted with dichloromethane. The combined organic phases are dried over anhydrous magnesium sulphate and concentrated. The residue is purified by chromatography on silica gel (ethyl acetate/heptane, 50:50). There is obtained 12 mg (38% yield) of a yellow solid (APCI+, 462, M+1). The compounds described in the following table 3 are prepared in a similar manner:

TABLE 3
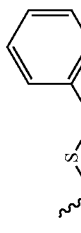
| N° | Q2 | G-Z | Y | Theoretical mass | Observed mass |
|---|---|---|---|---|---|
| 160 | 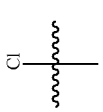 | 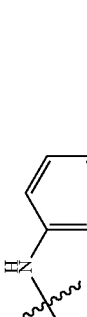 | Cl | 460 | 461(M+1) |
| 161 |  | 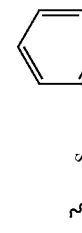 | Cl | 384 | 385(M+1) |
| 162 | 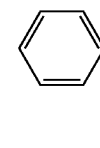 |  |  | 564 | |

TABLE 3-continued
| N° | Q2 | G-Z | Y | Theoretical mass | Observed mass |
|----|----|----|----|----|----|
| 163 | 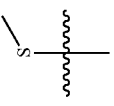 |  | 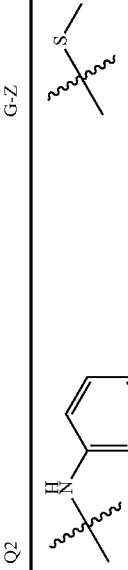 | 396 | |
| 164 | 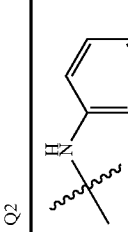 | 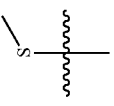 | 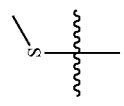 | 450 | |
| 165 |  | 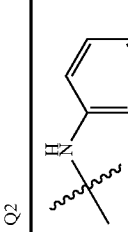 | 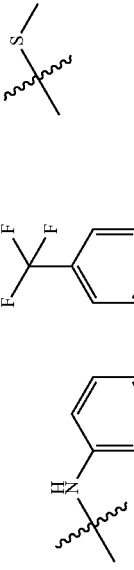 | 438 | |
| 166 | 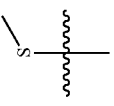 |  | 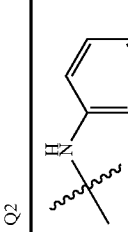 | 433 | 432(M − 1) |

TABLE 3-continued

| N° | Q2 | G-Z | Y | Theoretical mass | Observed mass |
|---|---|---|---|---|---|
| 167 | NH-C6H4-O-CH2-C6H5 | S-CH3 | NH-CH2-C6H5 | 455 | 456(M+1) |
| 168 | NH-C6H4-O-C6H4-CF3 | S-CH3 | NH-CH2-C6H5 | 509 | 510(M+1) |
| 169 | NH-C6H4-O-C6H4-CF3 | S-CH3 | N=N=N (azide) | 445 | |
| 170 | NH-C6H4-O-CH2-C6H5 | SH | Cl | 370 | 369(M−1) |

TABLE 3-continued
| N° | Q2 | G-Z | Y | Theoretical mass | Observed mass |
|---|---|---|---|---|---|
| 171 | 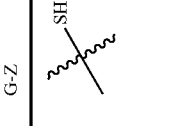 | 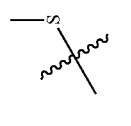 | 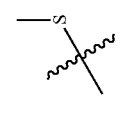 | 424 | 424(M+1) |
| 172 | 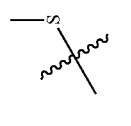 | 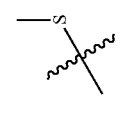 | 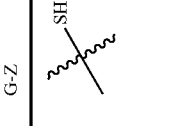 | 421 | 422(M+1) |
| 173 | 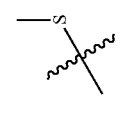 | 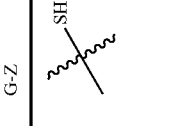 | 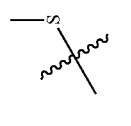 | 421 | |
| 174 | 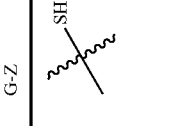 | 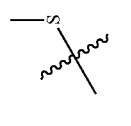 | 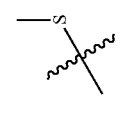 | 433 | |

TABLE 3-continued

| N° | Q2 | G-Z | Y | Theoretical mass | Observed mass |
|---|---|---|---|---|---|
| 175 | (4-benzyloxyphenyl)NH- | -S-CH3 | -N=N+=N- | 391 | 392(M+1) |
| 176 | (4-benzyloxyphenyl)NH- | -S-CH3 | -NH-propyl | 407 | 408(M+1) |
| 177 | (4-benzyloxyphenyl)NH- | -S-C(O)CH3 | Cl | 412 | 413(M+1) |
| 178 | [4-(3-trifluoromethylphenoxy)phenyl]NH- | -S-propyl | Cl | 466 | 467(M+1) |

TABLE 3-continued

| N° | Q2 | G-Z | Y | Theoretical mass | Observed mass |
|---|---|---|---|---|---|
| 179 | 3-(trifluoromethyl)phenoxy-phenyl-NH- | butyl-S- | Cl | 480 | 479(M−1) |
| 180 | 3-(trifluoromethyl)phenoxy-phenyl-NH- | allyl-S- | Cl | 464 | 465(M+1) |
| 181 | 3-(trifluoromethyl)phenoxy-phenyl-NH- | benzyl-S- | Cl | 514 | 515(M+1) |
| 182 | 3-(trifluoromethyl)phenoxy-phenyl-NH- | acetyl-S- | Cl | 466 | |

TABLE 3-continued

| N° | Q2 | G-Z | Y | Theoretical mass | Observed mass |
|---|---|---|---|---|---|
| 183 | 3-CF3-phenyl-O-4-phenyl-NH- | ethyl-S-C(CH3)2- | Cl | 452 | 453(M+1) |
| 184 | 3-CF3-phenyl-O-4-phenyl-NH- | isopropyl-S-C(CH3)2- | Cl | 466 | 467(M+1) |
| 185 | 4-CF3-phenyl-O-4-phenyl-NH- | methyl-S-C(CH3)2- | Cl | 438 | 439(M+1) |
| 186 | 3-CF3-phenyl-O-4-phenyl-NH- | 4-methoxybenzyl-S-C(CH3)2- | Cl | 544 | 545(M+1) |

TABLE 3-continued

| N° | Q2 | G-Z | Y | Theoretical mass | Observed mass |
|---|---|---|---|---|---|
| 187 | 3-(trifluoromethyl)phenoxy-phenyl-NH- | 4-methoxybenzyl-S- | methyl-NH- | 539 | 540(M+1) |
| 188 | 3-(trifluoromethyl)phenoxy-phenyl-NH- | 4-methoxybenzyl-S- | propyl-NH- | 567 | 568(M+1) |
| 189 | 3-(trifluoromethyl)phenoxy-phenyl-NH- | 4-methoxybenzyl-S- | butyl-NH- | 581 | 582(M+1) |
| 190 | 3-(trifluoromethyl)phenoxy-phenyl-NH- | 4-methoxybenzyl-S- | isobutyl-NH- | 581 | 582(M+1) |

TABLE 3-continued

| N° | Q2 | G-Z | Y | Theoretical mass | Observed mass |
|---|---|---|---|---|---|
| 191 | 3-CF3-phenyl-O-phenyl-NH- | 4-methoxybenzyl-S-C(CH3)2- | piperidin-1-yl-C(CH3)2- | 593 | 592(M − 1) |
| 192 | 3-CF3-phenyl-O-phenyl-NH- | 4-methoxybenzyl-S-C(CH3)2- | pyrrolidin-1-yl-C(CH3)2- | 579 | 580(M + 1) |
| 193 | 3-CF3-phenyl-O-phenyl-NH- | 4-methoxybenzyl-S-C(CH3)2- | isopropyl-NH-C(CH3)2- | 567 | 568(M + 1) |
| 194 | 3-CF3-phenyl-O-phenyl-NH- | 4-methoxybenzyl-S-C(CH3)2- | dimethylamino-C(CH3)2- | 553 | 554(M + 1) |

TABLE 3-continued
| N° | Q2 | G-Z | Y | Theoretical mass | Observed mass |
|---|---|---|---|---|---|
| 195 | 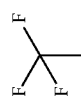 |  SH | 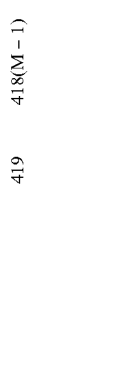 NH | 419 | 418(M − 1) |
| 196 |  | 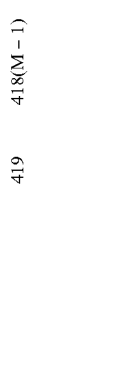 SH | 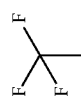 NH | 447 | 448(M + 1) |
| 197 | 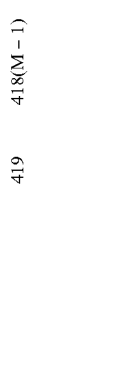 | 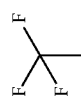 SH |  NH | 461 | |
| 198 | 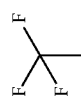 |  SH | 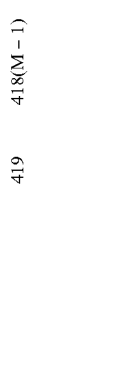 NH | 461 | 460(M − 1) |

TABLE 3-continued

| N° | Q2 | G-Z | Y | Theoretical mass | Observed mass |
|---|---|---|---|---|---|
| 199 | 3-CF3-phenyl-O-4-phenyl-NH- | 4-methoxybenzyl-S- | N=N=N-C(CH3)- | 551 | 552(M+1) |
| 200 | 3-CF3-phenyl-O-4-phenyl-NH- | 4-methoxybenzyl-S- | ethyl-NH- | 553 | 554(M+1) |
| 201 | 3-CF3-phenyl-O-4-phenyl-NH- | 4-methoxybenzyl-S- | benzyl-NH- | 615 | 616(M+1) |
| 202 | 3-CF3-phenyl-O-4-phenyl-NH- | SH | piperidinyl- | 473 | |

TABLE 3-continued

| N° | Q2 | G-Z | Y | Theoretical mass | Observed mass |
|---|---|---|---|---|---|
| 203 | (NH-phenyl) | SH | Cl | 264 | 265(M+1) |
| 204 | (NH-C6H4-O-p-tolyl) | SH | Cl | 370 | 371(M+1) |
| 205 | (NH-C6H4-O-p-tolyl) | disulfide linked to pyridine amide with p-methoxyphenyl amide | Cl | 738 | 369(M/2) |
| 206 | (NH-C6H4-O-p-tolyl) | S-CH2-(4-methoxyphenyl) | Cl | 490 | 491(M+1) |
| 207 | (NH-C6H4-O-(3-CF3-phenyl)) | SH | NH2 | 405 | 404(M−1) |

TABLE 3-continued

| N° | Q2 | G-Z | Y | Theoretical mass | Observed mass |
|---|---|---|---|---|---|
| 208 | 4-(4-methylphenoxy)phenyl-NH- | -S-methyl | Cl | 384 | 385(M+1) |
| 209 | 4-(4-methylphenoxy)phenyl-NH- | -S-ethyl | Cl | 398 | 399(M+1) |
| 210 | 4-(4-methylphenoxy)phenyl-NH- | -S-propyl | Cl | 412 | 413(M+1) |
| 211 | 4-(4-methylphenoxy)phenyl-NH- | -S-isopropyl | Cl | 412 | 413(M+1) |
| 212 | 4-(4-methylphenoxy)phenyl-NH- | -S-butyl | Cl | 426 | 427(M+1) |

TABLE 3-continued

| N° | Q2 | G-Z | Y | Theoretical mass | Observed mass |
|---|---|---|---|---|---|
| 213 | 4-methylphenoxy-phenyl-NH- | benzyl-S-CH< | Cl | 460 | 461(M+1) |
| 214 | 4-methylphenoxy-phenyl-NH- | allyl-S-CH< | Cl | 410 | 411(M+1) |
| 215 | 4-methylphenoxy-phenyl-NH- | 4-methoxybenzyl-S-CH< | ethoxy | 500 | 501(M+1) |
| 216 | 4-methylphenoxy-phenyl-NH- | 4-methoxybenzyl-S-CH< | butyl-NH- | 527 | 528(M+1) |
| 217 | 4-methylphenoxy-phenyl-NH- | 4-methoxybenzyl-S-CH< | piperidin-1-yl | 539 | 554(M+1) |

TABLE 3-continued

| N° | Q2 | G-Z | Y | Theoretical mass | Observed mass |
|---|---|---|---|---|---|
| 218 | 4-methylphenyl-O-phenyl-NH- | 4-methoxybenzyl-S- | -NH-CH3 | 485 | 486(M+1) |
| 219 | 4-methylphenyl-O-phenyl-NH- | 4-methoxybenzyl-S- | -NH-iPr | 513 | 513(M+1) |
| 220 | 4-methylphenyl-O-phenyl-NH- | PhC(O)S- | Cl | 474 | 474(M+1) |

TABLE 3-continued
| N° | Q2 | G-Z | Y | Theoretical mass | Observed mass |
|---|---|---|---|---|---|
| 221 | 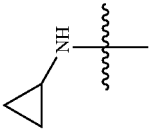 | 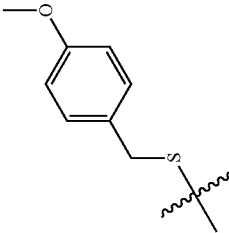 | 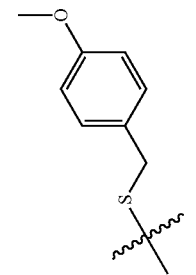 | 511 | 511(M+1) |
| 222 | 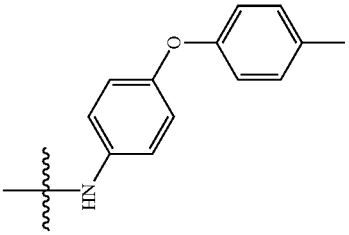 | 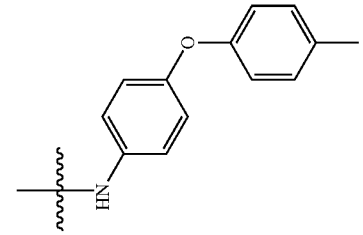 | 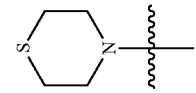 | 557 | 557(M+1) |

TABLE 3-continued

| N° | Q2 | G-Z | Y | Theoretical mass | Observed mass |
|---|---|---|---|---|---|
| 223 | 4-(4-methylphenoxy)phenyl-NH- | 4-methoxybenzyl-S-CH< | piperidinyl-CH<-piperidinyl | 539 | 540(M+1) |
| 224 | 4-(4-methylphenoxy)phenyl-NH- | 4-methoxybenzyl-S-CH< | piperidinyl-CH<-piperidinyl | 553 | 553(M+1) |
| 225 | 4-(4-methylphenoxy)phenyl-NH- | 4-methoxybenzyl-S-CH< | 3,5-dimethylpiperidinyl | 567 | 567(M+1) |

TABLE 3-continued
| N° | Q2 | G-Z | Y | Theoretical mass | Observed mass |
|---|---|---|---|---|---|
| 226 | 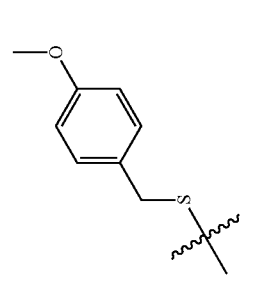 | 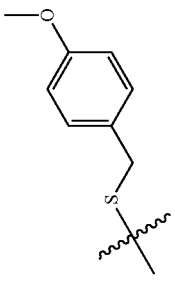 | 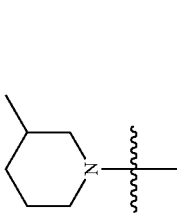 | 553 | 553(M + 1) |
| 227 | 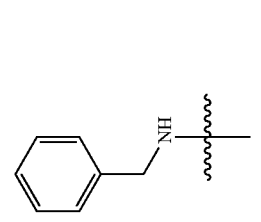 | 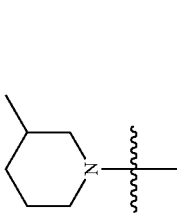 | 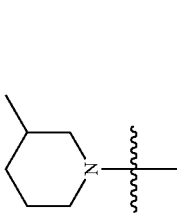 | 561 | 561(M + 1) |

TABLE 3-continued

| N° | Q2 | G-Z | Y | Theoretical mass | Observed mass |
|---|---|---|---|---|---|
| 228 | | | | 527 | 527(M+1) |
| 229 | | | | 513 | 513(M+1) |

TABLE 3-continued

| N° | Q2 | G-Z | Y | Theoretical mass | Observed mass |
|---|---|---|---|---|---|
| 230 | 4-(4-methylphenoxy)phenyl-NH- | 4-methoxybenzyl-S-CH2- | allyl-NH- | 511 | 511(M+1) |
| 231 | 4-(4-methylphenoxy)phenyl-NH- | 4-methoxybenzyl-S-CH2- | propyl-NH- | 513 | 513(M+1) |

TABLE 3-continued
| N° | Q2 | G-Z | Y | Theoretical mass | Observed mass |
|---|---|---|---|---|---|
| 232 | 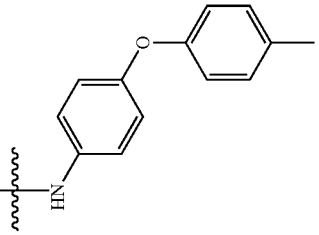 | 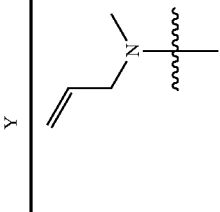 | 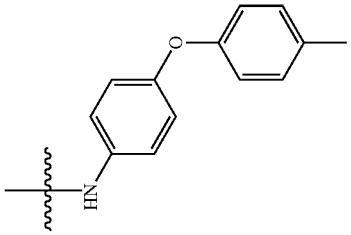 | 525 | 525(M + 1) |
| 233 | 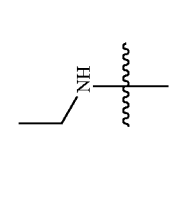 | | | 499 | 499(M + 1) |

TABLE 3-continued

| N° | Q2 | G-Z | Y | Theoretical mass | Observed mass |
|---|---|---|---|---|---|
| 234 | 4-methylphenyl-O-phenyl-NH- | 4-methoxybenzyl-S- | butyl-NH- | 527 | 528(M + 1) |
| 235 | 4-methylphenyl-O-phenyl-NH- | 4-methoxybenzyl-S- | -NO₂ | 501 | |
| 236 | 4-methylphenyl-O-phenyl-NH- | 4-methoxybenzyl-S- | -N₃ | 497 | 470(M + 1 − 28) |
| 237 | 4-methylphenyl-O-phenyl-NH- | HS- | 4-methylpiperidin-1-yl | 433 | 432(M − 1) |

TABLE 3-continued

| N° | Q2 | G-Z | Y | Theoretical mass | Observed mass |
|---|---|---|---|---|---|
| 238 | 4-methylphenoxy-phenyl-NH- | HS- | 3-methylpiperidin-1-yl | 433 | 432(M−1) |
| 239 | 4-methylphenoxy-phenyl-NH- | SH- | benzyl-NH- | 441 | 442(M+1) |
| 240 | 4-methylphenoxy-phenyl-NH- | SH- | allyl-NH- | 391 | 392(M+1) |
| 241 | 4-methylphenoxy-phenyl-NH- | SH- | propyl-NH- | 393 | 394(M+1) |

EXAMPLES OF BIOLOGICAL ACTIVITY OF THE COMPOUNDS OF THE INVENTION

Example A

In Vivo Test on *Alternaria Brassicae* (Leaf Spot of Crucifers)

An aqueous suspension, with a concentration of 2 g/L, of the active material tested is obtained by grinding it finely in the following mixture:
water
Tween 80 surfactant (polyoxyethylenated derivative of sorbitan oleate) diluted to 10% in water: 5 mL/mg of active material
clay: inert support q.s. 100%.

This aqueous suspension is then diluted with water so as to obtain the desired active material concentration.

Radish plants (Pernot variety) in starter cups, sown on a 50/50 peat soil-pozzolana substrate and grown at 18-20° C., are treated at the cotyledon stage by spraying with the aqueous suspension described above.

Plants, used as controls, are treated with an aqueous solution not containing the active material.

After 24 hours, the plants are contaminated by spraying them with an aqueous suspension of *Alternaria brassicae* spores (40,000 spores per $cm^3$). The spores are collected from a 12-13-day-old culture.

The contaminated radish plants are incubated for 6-7 days at about 18° C., under a humid atmosphere.

Grading is carried out 6 to 7 days after the contamination, in comparison with the control plants.

Under these conditions, good (at least 50%) or total protection is observed at a dose of 250 g/ha with the following compounds: 108, 110, 112, 115, 116, 130, 133.

Example B

In Vivo Test on *Septoria Nodorum* (Septoria Disease of Wheat)

An aqueous suspension, with a concentration of 2 g/L, of the active material tested is obtained by grinding it finely in the following mixture:
water
Tween 80 surfactant (polyoxyethylenated derivative of sorbitan oleate) diluted to 10% in water: 5 mL/mg of active material
clay: inert support q.s. 100%.

This aqueous suspension is then diluted with water so as to obtain the desired active material concentration.

Wheat plants (Scipion variety) in starter cups, sown on a 50/50 peat soil-pozzolana substrate and grown at 12° C., are treated at the 1-leaf stage (10 cm tall) by spraying them with the aqueous suspension described above.

Plants, used as controls, are treated with an aqueous solution not containing the active material.

After 24 hours, the plants are contaminated by spraying with an aqueous suspension of *Septoria nodorum* spores (500,000 spores per $cm^3$). The spores are collected from a seven-day-old culture.

The contaminated wheat plants are incubated for 72 hours at about 18° C., under a humid atmosphere, and then for 14 days at 90% relative humidity.

Grading is carried out 15 to 20 days after contamination, in comparison with the control plants.

Under these conditions, good (at least 50%) or total protection is observed, at a dose of 250 g/ha, with the following compounds: 108, 110, 112, 133.

Example C

In Vivo Test on *Magnaporthe Grisea* (Blast Disease of Rice)

An aqueous suspension, with a concentration of 50 mg/L, of the active material tested is obtained by grinding it finely in the following mixture:
water,
2% acetone.

Rice plants (Koshihirakari variety), sown on Kureha soil and grown in 33 $cm^2$ plastic pots up to the 3-4 leaf stage, are treated by spraying with the aqueous suspension described above.

Plants, used as controls, are treated with an aqueous solution not containing active material.

24 hours after treatment, the plants are contaminated by spraying with an aqueous suspension of *Magnaporthe grisea* spores (500,000 spores per $cm^3$).

The contaminated rice plants are placed in an incubator for 24 hours at 25° C. under a humid atmosphere, and then for 5 to 7 days in an incubation chamber at 20-25° C. and 70-90% relative humidity.

Grading is carried out 5 to 7 days after the contamination, by counting the lesions on the first leaf of the plant.

Under these conditions, good (at least 50%) or total protection is observed, at a dose of 50 mg/l, with the following compounds: 62, 114, 115.

Example D

In Vivo Test on *Erisyphe Graminis* f. Sp. Tritici (Powdery Mildew of Wheat)

An aqueous suspension, with a concentration of 2 g/L, of the active material tested is obtained by grinding it finely in the following mixture:
water
Tween 80 surfactant (polyoxyethylenated derivative of sorbitan oleate) diluted to 10% in water: 5 mL/mg of active material
clay: inert support q.s. 100%.

This aqueous suspension is then diluted with water so as to obtain the desired active material concentration.

Wheat plants (Audace variety) in starter cups, sown on 50/50 peat soil-pozzulana substrate and grown at 12° C., are treated at the 1-leaf stage (10 cm tall) by spraying with the aqueous suspension described above.

Plants, used as controls, are treated with an aqueous solution not containing the active material.

After 24 hours, the plants are contaminated by dusting them with *Erisyphe graminis* f. sp. tritici spores, the dusting being carried out using diseased plants.

Grading is carried out 7 to 14 days after the contamination, in comparison with the control plants.

Under these conditions, good (at least 50%) or total protection is observed, at a dose of 500 g/ha, with the compound described in Example: 108.

Example E

In Vivo Test on *Rhizoctonia Solani* (Bordered Sheath Spot of Rice)

An aqueous suspension, with a concentration of 100 mg/L, of the active material tested is obtained by grinding it finely in the following mixture:

water,

2% acetone.

Rice plants (Koshihirakari variety), sown on Kureha soil and grown in 33 cm² plastic pots up to the 7-8 leaf stage, are treated by spraying with the aqueous suspension described above.

Plants, used as controls, are treated with an aqueous solution not containing active material.

After 24 hours, each plant is contaminated by placing an agar disk of fungal growth, taken from a Rhizoctonia solani culture on PDA, between the stem and the sheath.

The contaminated plants are then incubated for 24 hours at 25° C. in an atmosphere at 100% humidity and then incubated for 5-7 days at a relative humidity of between 70-90%.

Grading is carried out 7 days after the contamination, by measuring the height of the lesion on the plant in comparison with the controls.

Under these conditions, good (at least 50%) protection is observed, at a dose of 100 ppm, with the compounds described as Example: 62, 133.

Example F

In Vivo Test on *Septoria Tritici* (Septoria Disease of Wheat)

An aqueous suspension, at a concentration of 1.5%, of the active material tested is obtained by grinding it finely in a formulation of concentrated suspension type, for example such as the one described in paragraph [0061] above (formulation CS1, CS2 or CS3).

This aqueous suspension is then diluted in water so as to obtain the desired active material concentration, i.e. 2 g/L.

Wheat plants (Scipion variety) in starter cups, sown on a 50/50 peat soil-pozzolana substrate and grown at 12° C., are treated at the 1-leaf stage (10 cm tall) by spraying with the aqueous suspension described above.

Plants, used as controls, are treated with an aqueous solution not containing the active material.

After 24 hours, the plants are contaminated by spraying them with an aqueous suspension of *Septoria tritici* spores (500,000 spores per mL). The spores are collected from a 15-day-old culture and are suspended in a nutrient solution composed of:

1.5 g/L of gelatin 0.5 g/L of sodium oleate 24 g/L of PDB

The contaminated wheat plants are incubated for 72 hours at about 20° C. and at 100% relative humidity, and then for 15 days at 80% relative humidity.

Grading is carried out 15 to 20 days after the contamination, in comparison with the control plants. Under these conditions, good (at least 50%) protection is observed, at a dose of 500 g/ha, with the compounds described as Example: 108.

The invention claimed is:

1. A compound of general formula (I):

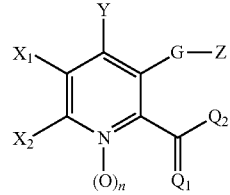

in which:

G represents an oxygen or sulphur atom, n represents 0 or 1, $Q_1$ is selected from the group consisting of an oxygen atom and a sulphur atom, $Q_2$ represents a group —$NR_4R_5$, wherein $R_4$ represents a hydrogen atom and $R_5$ is selected from the group consisting of aryl, arylalkyl, heterocyclyl and heterocyclylalkyl, optionally substituted with one or more radicals $R_9$ and/or aryl and/or arylalkyl, which may be identical or different, and/or a group -T'-$R_8$;

with the proviso that $Q_2$ is not

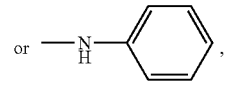

$Q_1$ and $Q_2$ may together form a ring of 5 to 7 atoms consisting of 2 to 3 oxygen and/or nitrogen atoms, optionally substituted with one or more radicals, which may be identical or different, chosen from halogens and alkyl and haloalkyl radicals, wherein, when $R_5$ is heterocyclyl or heterocyclylalkyl, the term "heterocycle" is defined as a moiety selected from the group consisting of:

a 5-membered ring of formula (i):

in which each B is independently selected from the group consisting of carbon, nitrogen, oxygen and sulphur atoms such that the group comprises from 0 to 3 carbon atoms, from 0 to 1 sulphur atom, from 0 to 1 oxygen atom and from 0 to 4 nitrogen atoms;

a 6-membered ring of formula (ii):

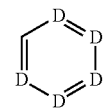

in which each D is independently selected from the group consisting of carbon and nitrogen atoms such that the group comprises from 1 to 4 carbon atoms and from 1 to 4 nitrogen atoms;

two 6-membered fused rings of formula (iii):

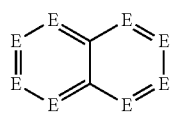

(iii)

in which each E is independently selected from the group consisting of carbon and nitrogen atoms such that the said group comprises from 4 to 7 carbon atoms and from 1 to 4 nitrogen atoms;

a 6-membered ring and a 5-membered ring fused together of formula (iv):

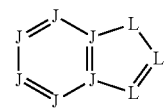

(iv)

in which:
each J is independently selected from the group consisting of carbon and nitrogen atoms such that the group comprises from 3 to 6 carbon atoms and from 0 to 3 nitrogen atoms, and each L is independently selected from the group consisting of carbon, nitrogen, oxygen and sulphur atoms such that said group comprises from 0 to 3 carbon atoms, from 0 to 1 sulphur atom, from 0 to 1 oxygen atom and from 0 to 3 nitrogen atoms, and the two fused rings comprise a total of from 3 to 8 carbon atoms;

two 5-membered fused rings of formula (v)

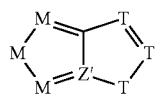

(v)

in which:
each M is independently selected from the group consisting of carbon, nitrogen, oxygen and sulphur atoms such that said group comprises from 0 to 3 carbon atoms, from 0 to 1 sulphur atom, from 0 to 1 oxygen atom and from 0 to 3 nitrogen atoms, each T is independently selected from the group consisting of carbon, nitrogen, oxygen and sulphur atoms such that said group comprises from 0 to 3 carbon atoms, from 0 to 1 sulphur atom, from 0 to 1 oxygen atom and from 0 to 3 nitrogen atoms, and the combination of Zs and Ts is selected such that together they comprise a total of from 0 to 6 carbon atoms, and Z' is selected from the group consisting of a carbon atom and a nitrogen atom;

Z is selected from the group consisting of a hydrogen atom, a cyano radical and an alkyl, allyl, aryl, arylalkyl, propargyl, cycloalkyl, halocycloalkyl, alkenyl, alkynyl, cyanoalkyl, haloalkyl, alkoxyalkyl, haloalkoxyalkyl, alkylthioalkyl, haloalkylthioalkyl, N-alkylaminoalkyl, N,N-dialkylaminoalkyl, acylaminoalkyl, alkoxycarbonylaminoalkyl, aminocarbonylaminoalkyl, alkoxycarbonyl, N-alkylaminocarbonyl, N,N-dialkylaminocarbonyl, acyl, thioacyl, alkoxythiocarbonyl, N-alkylaminothiocarbonyl, N,N-dialkylaminothiocarbonyl, alkylsulphinyl, haloalkylsulphinyl, alkylsulphonyl, haloalkylsulphonyl, alkoxysulphonyl, aminosulphonyl, N-alkylaminosulphonyl, N,N-dialkylaminosulphonyl, arylsulphinyl, arylsulphonyl, aryloxysulphonyl, N-arylaminosulphonyl, N,N-diarylaminosulphonyl or N,N-arylalkylaminosulphonyl radical;

Y is selected from the group consisting of a halogen atom, a hydroxyl, mercapto, nitro, thiocyanato, azido, cyano or pentafluorosulphonyl radical, an alkyl, haloalkyl, alkylthio, haloalkylthio, alkoxyalkyl, haloalkoxyalkyl, alkylthioalkyl, haloalkylthioalkyl, cyanoalkyl, cyanoalkoxy, cyanoalkylthio, alkylsulphinyl, haloalkylsulphinyl, alkylsulphonyl, haloalkylsulphonyl or alkoxysulphonyl radical, a cycloalkyl, halocycloalkyl, alkenyl, alkynyl, alkenyloxy, alkynyloxy, alkenylthio or alkynylthio group, an amino, N-alkylamino, N,N-dialkylamino, —NHCOR$_{10}$, —NHCSR$_{10}$, N-alkylaminocarbonylamino, N,N-dialkylaminocarbonylamino, aminoalkyl, N-alkylaminoalkyl, N,N-dialkylaminoalkyl, acylaminoalkyl, thioacylamino, alkoxythiocarbonylamino, N-alkylaminothiocarbonylamino, N,N-dialkylaminothiocarbonylamino, N,N-arylalkylaminocarbonylamino, N-alkylsulphinylamino, N-alkylsulphonylamino, N-alkyl(alkylsulphonyl)amino, N-arylsulphinylamino, N-arylsulphonylamino, N-alkoxysulphonylamino, N-alkoxysulphinylamino, N-haloalkoxysulphinylamino, N-haloalkoxysulphonylamino, N-arylamino, N,N-diarylamino, arylcarbonylamino, alkoxycarbonylamino, N-arylaminocarbonylamino, N,N-diarylaminocarbonylamino, arylthiocarbonylamino, aryloxythiocarbonylamino, N-arylaminothiocarbonylamino, N,N-diarylaminothiocarbonylamino or N,N-arylalkylaminothiocarbonylamino group, an acyl, carboxyl, carbamoyl, N-alkylcarbamoyl, N,N-dialkylcarbamoyl, lower alkoxycarbonyl, N-arylcarbamoyl, N,N-diarylcarbamoyl, aryloxycarbonyl or N,N-arylalkylcarbamoyl radical, and an imino group of formula:

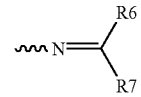

$X_1$ and $X_2$ are identical or different and are independently selected from the group consisting of a hydrogen atom, a halogen atom, a hydroxyl, mercapto, nitro, thiocyanato, azido, cyano or pentafluorosulphonyl radical, and an alkyl, haloalkyl, alkoxy, haloalkoxy, alkylthio, haloalkylthio, alkoxyalkyl, haloalkoxyalkyl, alkylthioalkyl, haloalkylthioalkyl, cyanoalkyl, cyanoalkoxy, cyanoalkylthio, alkylsulphinyl, haloalkylsulphinyl, alkylsulphonyl, haloalkylsulphonyl or alkoxysulphonyl radical, or $X_1$ and $X_2$ may also be joined together, thus forming a saturated, partially unsaturated or totally unsaturated 4- to 8-membered ring optionally comprising one or more hetero atoms chosen from sulphur, oxygen, nitrogen and phosphorus, $R_1$, $R_6$ and $R_7$ are identical or different and are independently selected from the group consisting of a hydrogen atom, an optionally substituted alkyl radical comprising from 1 to 12 carbon atoms in a linear or branched chain, a haloalkyl, cycloalkyl, halocycloalkyl, alkoxy, aryloxy, arylalkoxy, haloalkoxy, alkylthio, haloalkylthio, alkoxyalkyl, haloalkoxyalkyl, alkylthioalkyl, haloalkylthioalkyl, cyanoalkyl or acyl radical, a nitro, cyano, carboxyl, carbamoyl or 3-oxetanyloxycarbonyl radical, and an N-alkylcarbamoyl, N,N-dialkylcarbamoyl, alkoxycarbonyl, alkylthiocarbonyl, haloalkoxycarbonyl, alkoxythiocarbonyl, haloalkoxythiocarbonyl, alkylthiothiocarbonyl, alkenyl, alkynyl, N-alkylamino, N,N-dialkylamino, N-alkylaminoalkyl or N,N-dialkylaminoalkyl radical, or a radical chosen from aryl, arylalkyl, heterocyclyl and heterocyclylalkyl, optionally substituted with one or more radicals $R_9$ and/or aryl and/or arylalkyl, which may be identical or different, and/or a group -T'-$R_8$, or $R_6$ and $R_7$ may be joined together, thus forming a saturated, partially unsaturated or totally unsaturated 4- to 8-membered ring optionally comprising one or more hetero atoms chosen from sulphur, oxygen, nitrogen and phosphorus, T' represents a direct bond or a divalent radical selected from the group consisting of a radical —$(CH_2)_m$—, m taking a value between 1 and 12, limits included, the said radical optionally being interrupted or ending with one or two heteroatoms chosen from nitrogen, oxygen and/or sulphur, and an oxyalkylene, alkoxyalkylene, carbonyl (—CO—), oxycarbonyl (—O—CO—), carbonyloxy (—CO—O—), sulphinyl (—SO—), sulphonyl (—$SO_2$—), oxysulphonyl (—O—$SO_2$—), sulphonyloxy (—$SO_2$—O—), oxysulphinyl (—O—SO—), sulphinyloxy (—SO—O—), thio (—S—), oxy (—O—), vinyl (—C=C—), ethynyl —C≡C—, —$NR_9$—, —$NR_9$O—, —O$NR_9$—, —N=N—, —$NR_9$—$NR_{10}$—, —$NR_9$—S—, —$NR_9$—SO—, —$NR_9$—$SO_2$—, —S—$NR_9$—, —SO—$NR_9$—, —$SO_2$—$NR_9$—, —CO—$NR_9$—O— or —O—$NR_9$—CO— radical, $R_8$ is selected from the group consisting of a hydrogen atom and an aryl or heterocyclyl radical, $R_9$ and $R_{10}$, which may be identical or different, are independently selected from the group consisting of a hydrogen atom, a halogen atom, a hydroxyl, mercapto, nitro, thiocyanato, azido, cyano or pentafluorosulphonyl radical, and an alkyl, haloalkyl, alkoxy, haloalkoxy, alkylthio, haloalkylthio, alkoxyalkyl, haloalkoxyalkyl, alkylthioalkyl, haloalkylthioalkyl, arylalkyl, cyanoalkyl, cyanoalkoxy, cyanoalkylthio, alkylsulphinyl, haloalkylsulphinyl, alkylsulphonyl, haloalkylsulphonyl or alkoxysulphonyl radical, or wherein said compound is a geometrical or optical isomer, an enantiomer or diastereoisomer, a tautomeric form, a salt or a metal or metalloid complex of the compound of formula (I) as defined above.

2. The compound of claim 1 wherein:
$X_1$ and $X_2$ each represent a hydrogen atom.

3. The compound of claim 1 wherein:
Z is selected from the group consisting of an alkyl radical and a hydrogen atom or an alkoxyalkyl, haloalkoxyalkyl, alkylthioalkyl, haloalkylthioalkyl, N-alkylaminoalkyl, N,N-dialkylaminoalkyl, acylaminoalkyl, acyl, thioacyl, cyanoalkyl, alkoxythiocarbonyl, N-alkylaminothiocarbonyl, N,N-dialkylaminothiocarbonyl or alkylsulphinyl radical.

4. The compound of claim 1 wherein:
Y is selected from the group consisting of a halogen atom, a hydroxyl, mercapto, nitro, thiocyanato, azido, cyano or pentafluorosulphonyl radical, an alkyl, haloalkyl, alkylthio, haloalkylthio, alkoxyalkyl, haloalkoxyalkyl, alkylthioalkyl, haloalkylthioalkyl, alkylsulphinyl, haloalkylsulphinyl, alkylsulphonyl, haloalkylsulphonyl or alkoxysulphonyl radical, an amino group, and an N-alkylamino, N,N-dialkylamino, —$NHCOR_{10}$, —$NHCSR_{10}$, N-arylamino, N,N-diarylamino, arylcarbonylamino, arylthiocarbonylamino, aryloxythiocarbonylamino or N,N-arylalkylaminothiocarbonylamino group.

5. The compound of claim 1 wherein:
$X_1$ and $X_2$ each represent a hydrogen atom,
Z is selected from the group consisting of an alkyl radical, a hydrogen atom, an alkoxyalkyl, haloalkoxyalkyl, alkylthioalkyl, haloalkylthioalkyl, N-alkylaminoalkyl, N,N-dialkylaminoalkyl, acylaminoalkyl, acyl, thioacyl, cyanoalkyl, alkoxythiocarbonyl, N-alkylaminothiocarbonyl, N,N-dialkylaminothiocarbonyl and an alkylsulphinyl radical, and
Y is from the group consisting of a halogen atom, a hydroxyl, mercapto, nitro, thiocyanato, azido, cyano or pentafluorosulphonyl radical, an alkyl, haloalkyl, alkylthio, haloalkylthio, alkoxyalkyl, haloalkoxyalkyl, alkylthioalkyl, haloalkylthioalkyl, alkylsulphinyl, haloalkylsulphinyl, alkylsulphonyl, haloalkylsulphonyl or alkoxysulphonyl radical, an amino group, and an N-alkylamino, N,N-dialkylamino, —$NHCOR_{10}$, —$NHCSR_{10}$, N-arylamino, N,N-diarylamino, arylcarbonylamino, arylthiocarbonylamino, aryloxythiocarbonylamino or N,N-arylalkylaminothiocarbonylamino group.

6. The compound of claim 1 wherein:
$X_1$ and $X_2$ each represent a hydrogen atom,
Z is selected from the group consisting of an alkyl radical, a hydrogen atom, an alkoxyalkyl, haloalkoxyalkyl, alkylthioalkyl, haloalkylthioalkyl, N-alkylaminoalkyl, N,N-dialkylaminoalkyl, acylaminoalkyl, acyl, thioacyl, cyanoalkyl, alkoxythiocarbonyl, N-alkylaminothiocarbonyl, N,N-dialkylaminothiocarbonyl and an alkylsulphinyl radical,
Y is selected from the group consisting of a halogen atom, a hydroxyl, azido, alkylthio and alkylsulphonyl radical and an amino, —$NHCOR_{10}$ and —$NHCSR_{10}$ group, and
$Q_1$ represents an oxygen atom.

7. A compound selected from the group consisting of:
4-amino-3-hydroxy-N-[4-(4-methylphenoxy)phenyl]-2-pyridinecarboxamide,
4-(formylamino)-3-hydroxy-N-{4-[3-(trifluoromethyl)phenoxy]phenyl}-2-pyridinecarboxamide,
4-amino-3-hydroxy-N-{4-[4-(trifluoromethyl)phenoxy]phenyl}-2-pyridinecarboxamide,
N-[4-(4-chlorophenoxy)phenyl]-4-(formylamino)-3-hydroxy-2-pyridinecarboxamide,
4-(formylamino)-3-hydroxy-N-{4-[4-(trifluoromethyl)phenoxy]phenyl}-2-pyridinecarboxamide, and
N-[4-(benzyloxy)phenyl]-4-(formylamino)-3-hydroxy-2-pyridinecarboxamide, or wherein said compound is a geometrical or optical isomer, an enantiomer or diastereoisomer, a tautomeric form, a salt or a metal or metalloid complex thereof.

8. A fungicidal composition comprising, as active material, an effective amount of at least one compound according to claim 1, or wherein said compound is a geometrical or optical isomer, an enantiomer or diastereoisomer, a tautomeric form, a salt or a metal or metalloid complex thereof, that is agriculturally acceptable.

9. The fungicidal composition of claim 8 further comprising an agriculturally acceptable solid or liquid support and/or a surfactant which is also agriculturally acceptable, as well as, optionally, one or more other fungicides, insecticides, herbicides, acaricides, attractants or pheromones and other compounds with biological activity.

10. The fungicidal composition of claim 8 comprising from 0.05 to 99% by weight of active material.

11. A fungicidal composition comprising, as active material, an effective amount of at least one compound according to claim 7, or wherein said compound is a geometrical or optical isomer, an enantiomer or diastereoisomer, a tautomeric form, a salt or a metal or metalloid complex thereof, that is agriculturally acceptable.

12. The fungicidal composition claim 11 further comprising an agriculturally acceptable solid or liquid support and/or a surfactant which is also agriculturally acceptable, as well as, optionally, one or more other fungicides, insecticides, herbicides, acaricides, attractants or pheromones and other compounds with biological activity.

13. The fungicidal composition of claim 11 comprising from 0.05 to 99% by weight of active material.

* * * * *